United States Patent
Kobayashi et al.

(10) Patent No.: US 9,903,865 B2
(45) Date of Patent: Feb. 27, 2018

(54) ASSAY, IMMUNOCHROMATOGRAPHIC TEST STRIP, AND ASSAY REAGENT KIT FOR MEASURING AN ANALYTE, USING A HEMATOCRIT CORRECTION

(75) Inventors: Koji Kobayashi, Ryugasaki (JP); Motoki Morita, Ryugasaki (JP); Sachiko Ito, Ryugasaki (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 380 days.

(21) Appl. No.: 13/638,544

(22) PCT Filed: Mar. 31, 2011

(86) PCT No.: PCT/JP2011/058288
§ 371 (c)(1),
(2), (4) Date: Oct. 31, 2012

(87) PCT Pub. No.: WO2011/125877
PCT Pub. Date: Oct. 13, 2011

(65) Prior Publication Data
US 2013/0052655 A1 Feb. 28, 2013

(30) Foreign Application Priority Data

Mar. 31, 2010 (JP) ................................ 2010-082928
Mar. 31, 2010 (JP) ................................ 2010-082929

(51) Int. Cl.
*G01N 33/558* (2006.01)
*G01N 33/72* (2006.01)

(52) U.S. Cl.
CPC ......... *G01N 33/558* (2013.01); *G01N 33/721* (2013.01); *G01N 2333/4737* (2013.01); *G01N 2333/805* (2013.01)

(58) Field of Classification Search
None
See application file for complete search history.

(56) References Cited

U.S. PATENT DOCUMENTS

| 6,184,042 B1 | 2/2001 | Neumann et al. |
| 6,214,629 B1 * | 4/2001 | Freitag et al. ................ 436/518 |
| 6,262,264 B1 * | 7/2001 | Buck, Jr. ............ C07F 15/0026 205/792 |
| 6,309,888 B1 * | 10/2001 | Holvoet ............. G01N 33/6893 435/7.1 |

(Continued)

FOREIGN PATENT DOCUMENTS

| EP | 0724156 A1 | 7/1996 |
| JP | 8-94618 A | 4/1996 |

(Continued)

OTHER PUBLICATIONS

English translation of International Preliminary Report on Patentability and Written Opinion dated Nov. 22. 2012, in PCT International Application No. PCT/JP2011/058288.

(Continued)

*Primary Examiner* — Scott Long
*Assistant Examiner* — Gary E Hollinden
(74) *Attorney, Agent, or Firm* — Birch, Stewart, Kolasch & Birch, LLP

(57) ABSTRACT

The present invention provides a measurement method utilizing immunochromatography, an immunochromatographic test strip, and a reagent kit of immunochromatography capable of accurate short-time measurement of an analyte in blood with simple operations as compared to the conventional methods. The present invention provides a method of measurement by immunochromatography in which concentrations of an analyte and hemoglobin in the same sample are measured by immunochromatography to perform hematocrit correction of a measurement value of the analyte by using a measurement value of hemoglobin, as well as a test strip and a reagent kit for immunochromatography.

26 Claims, 11 Drawing Sheets

(56) References Cited

U.S. PATENT DOCUMENTS

| | | | | |
|---|---|---|---|---|
| 7,379,167 | B2* | 5/2008 | Mawhirt | B01L 3/5023 356/39 |
| 7,479,393 | B2* | 1/2009 | Noetzel | B01L 3/502746 422/504 |
| 8,568,999 | B2* | 10/2013 | Hansson | G01N 33/689 435/7.92 |
| 9,097,728 | B2* | 8/2015 | Baudin-Creuza | G01N 33/721 |
| 9,103,838 | B2* | 8/2015 | Geiger | G01N 33/721 |
| 2003/0068665 | A1 | 4/2003 | Kawamura et al. | |
| 2003/0100128 | A1* | 5/2003 | Kenjyou et al. | 436/518 |
| 2004/0191124 | A1* | 9/2004 | Noetzel et al. | 422/69 |
| 2004/0197820 | A1 | 10/2004 | Wei et al. | |
| 2006/0246601 | A1* | 11/2006 | Song et al. | 436/514 |
| 2008/0113382 | A1* | 5/2008 | Chandler | C12Q 1/28 435/7.1 |
| 2011/0070634 | A1* | 3/2011 | Takahashi et al. | 435/287.7 |

FOREIGN PATENT DOCUMENTS

| | | |
|---|---|---|
| JP | 8-262024 A | 10/1996 |
| JP | 11-38006 A | 2/1999 |
| JP | 2000-46831 A | 2/2000 |
| JP | 2002-530651 A | 9/2002 |
| JP | 2003-161733 A | 6/2003 |
| JP | 2004-85425 A | 3/2004 |
| JP | 2004-132892 A | 4/2004 |
| JP | 2006-38700 A | 2/2006 |
| JP | 2008-539424 A | 11/2008 |
| WO | WO 00/29852 A1 | 5/2000 |
| WO | WO 02/052265 A1 | 7/2002 |
| WO | WO 2004/095030 A1 | 11/2004 |
| WO | WO 2006/041537 A1 | 4/2006 |
| WO | WO 2008098734 A1 * 8/2008 ........... G01N 33/689 |  |
| WO | WO 2009/144894 A1 | 12/2009 |
| WO | WO 2010/001598 A1 | 1/2010 |

OTHER PUBLICATIONS

Extended European Search Report dated Aug. 8, 2013, in European Patent Application No. 11765777.5.

International Search Report for PCT/JP2011/058288 dated May 24, 2011.

* cited by examiner

[Fig.1]
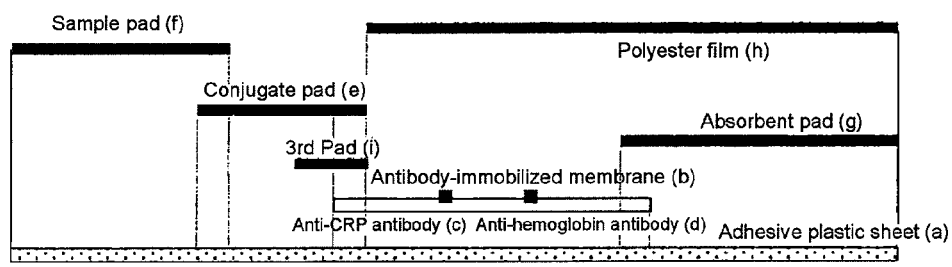
[Fig.2]
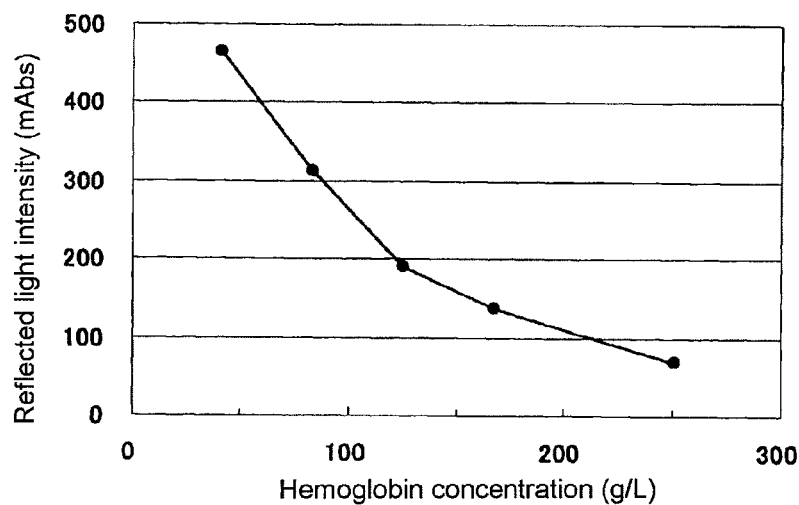
Hemoglobin measurement by sandwich immunochromatography utilizing competitive reaction

[Fig.3]
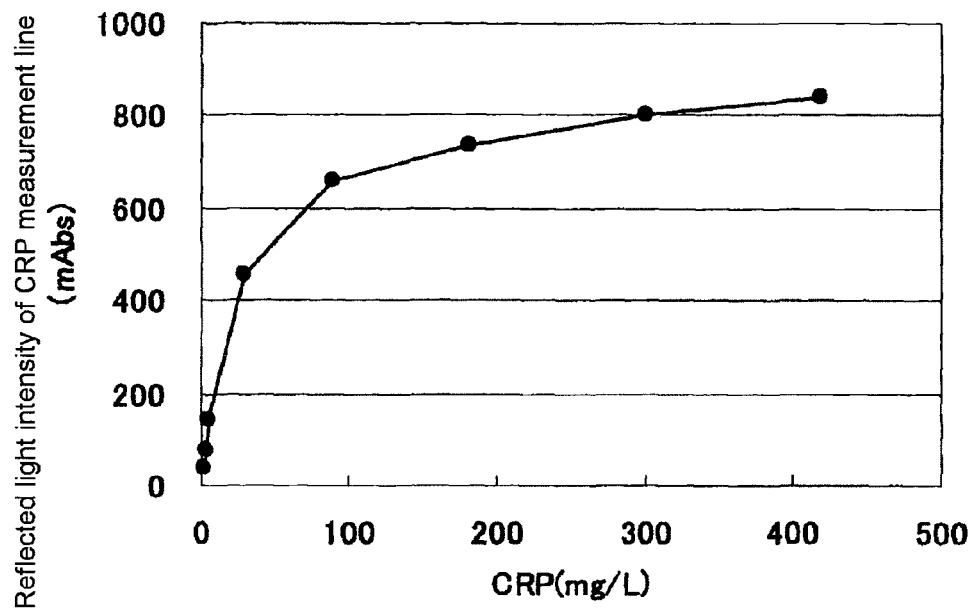
Calibration curve in CRP measurement of the present method

[Fig.4]
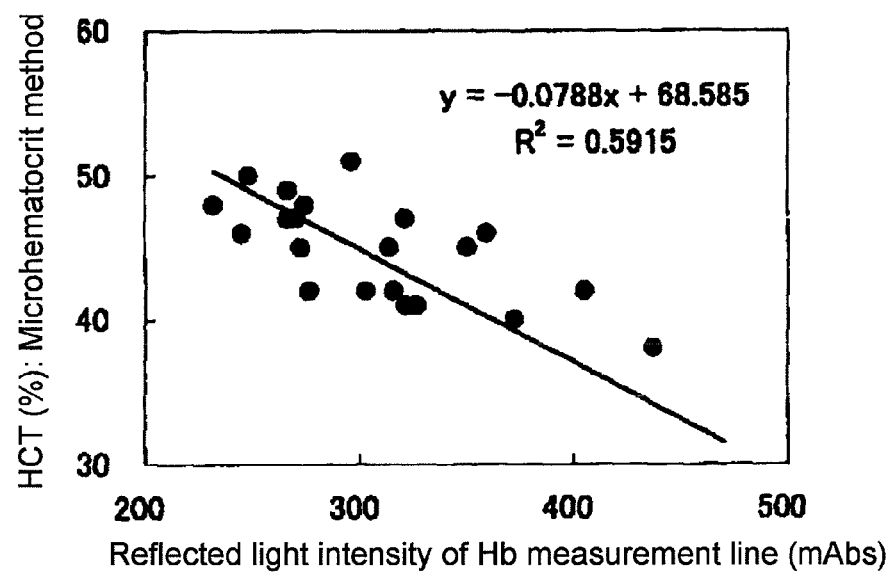
Relationship between reflected light intensity of Hb measurement line and hematocrit value of the present invention

[Fig.5]
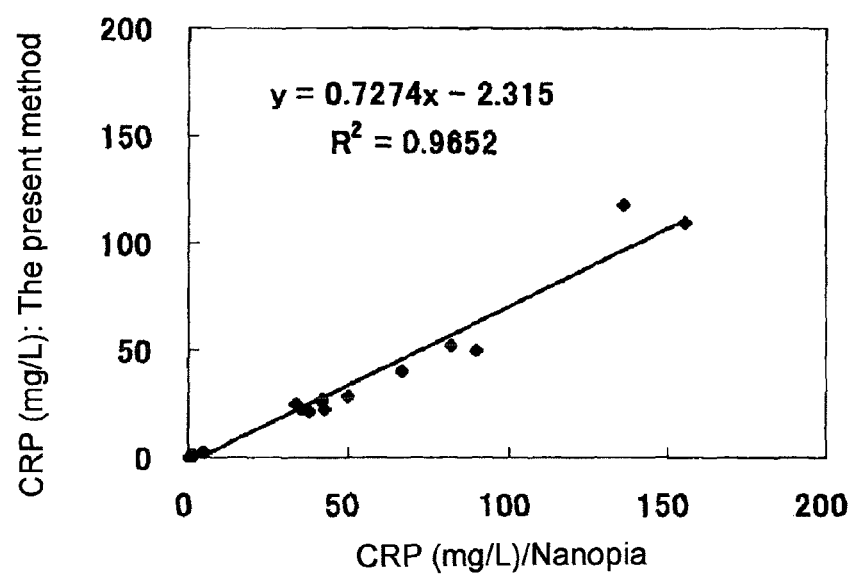
Correlation between commercially available CRP measurement kit (Nanopia CRP) and the present method when HCT correction is not performed

[Fig.6]
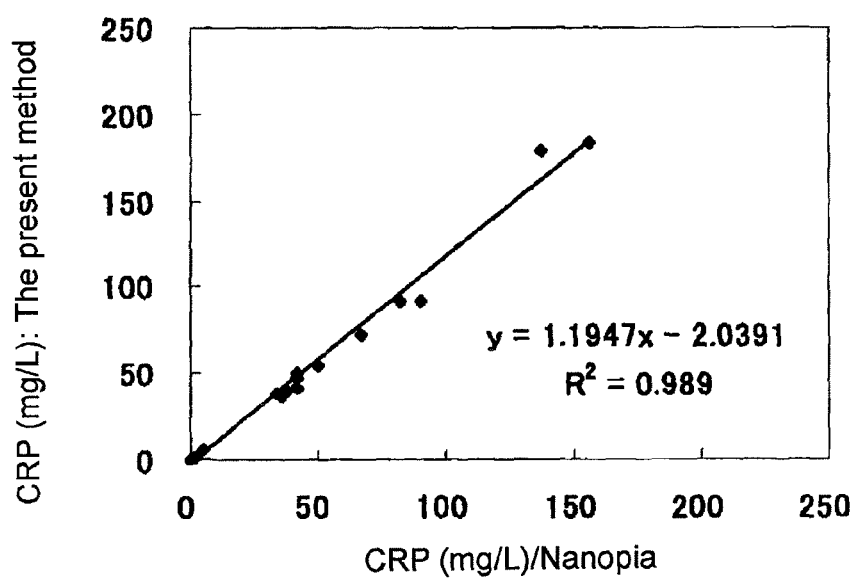
Correlation between commercially available CRP measurement kit (Nanopia CRP) and the present method when HCT correction is performed

[Fig.7]
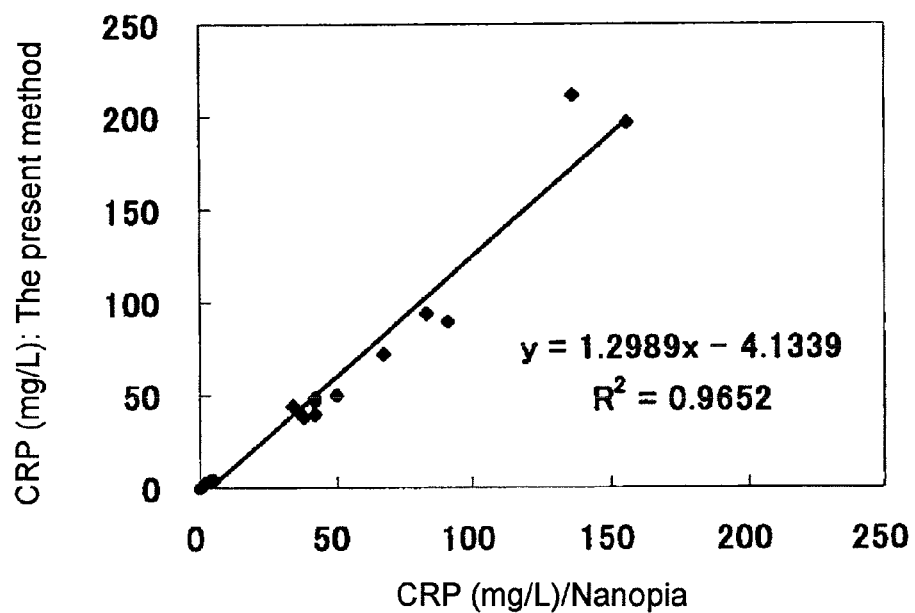
Correlation between commercially available CRP measurement kit (Nanopia CRP) and the present method when average HCT (44 %) uniform correction is performed

[Fig.8]
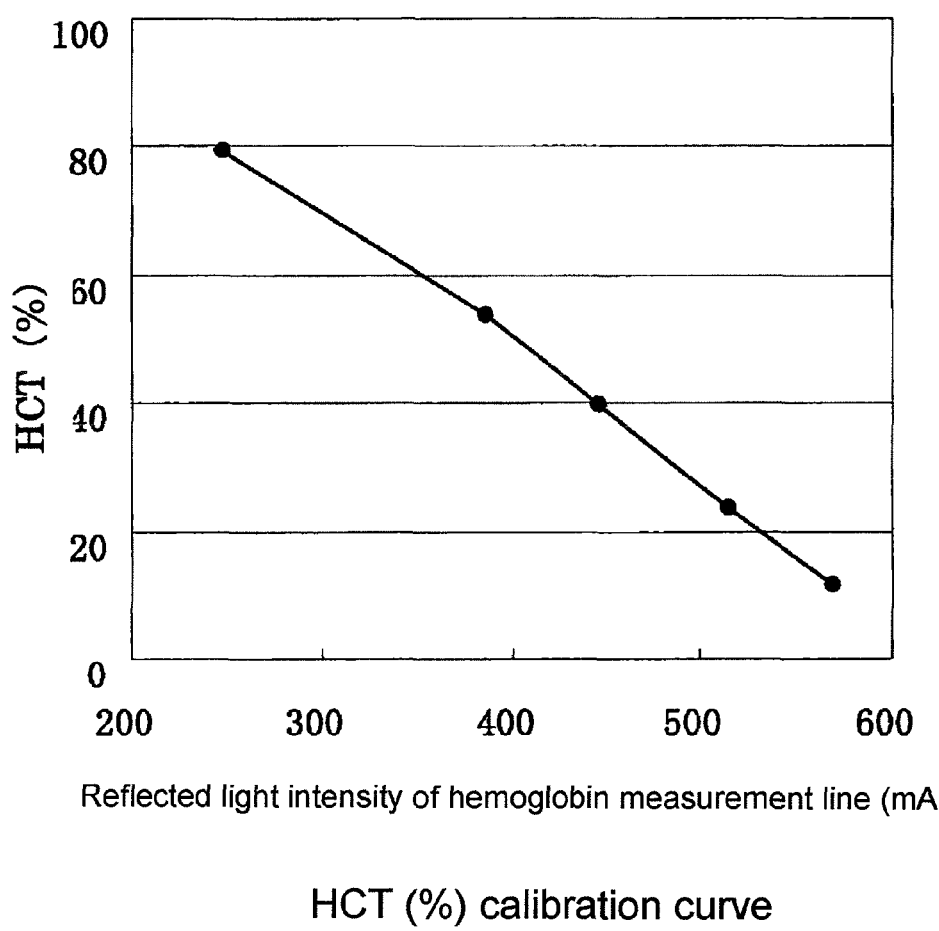
HCT (%) calibration curve

[Fig.9]
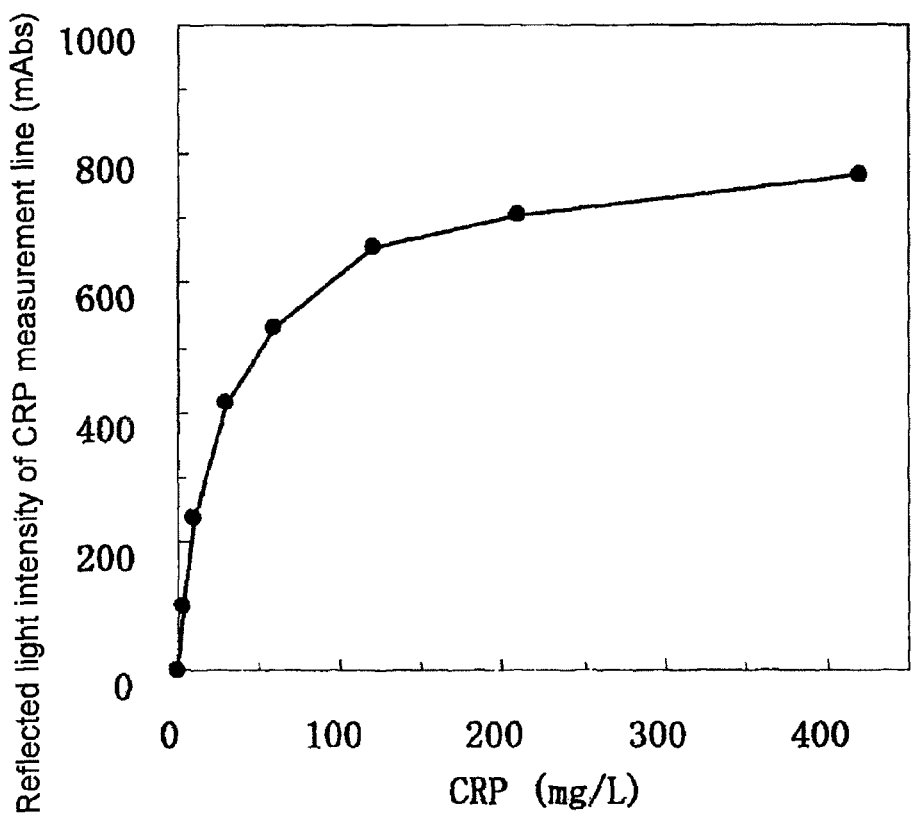
CRP measurement calibration curve

[Fig.10]
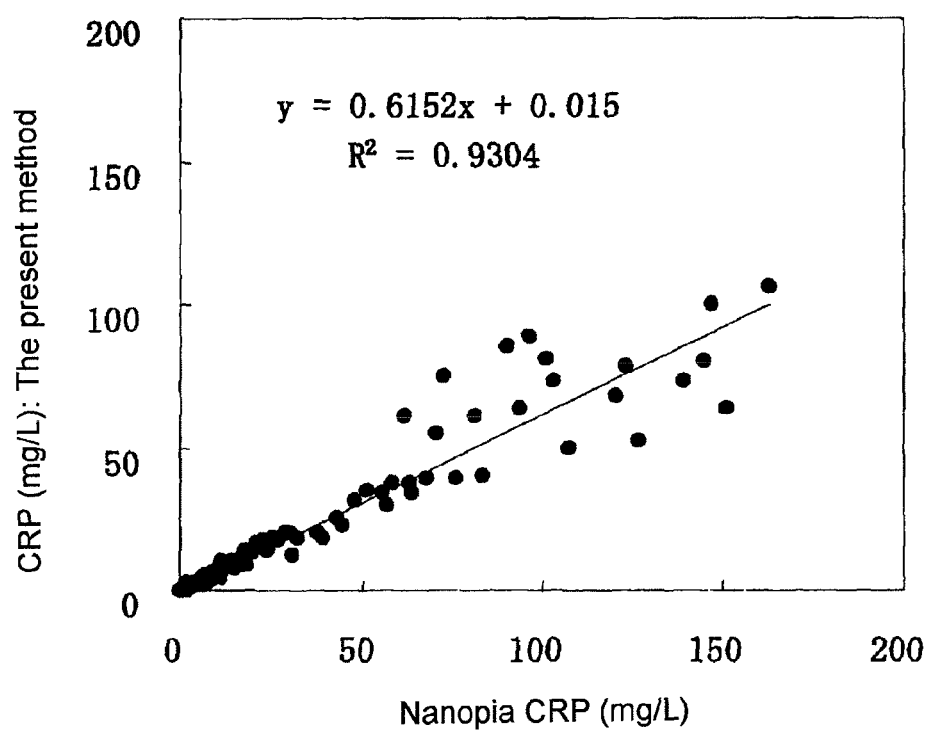
Correlation between commercially available CRP measurement kit (Nanopia CRP) and the present method when HCT correction is not performed

[Fig.11]
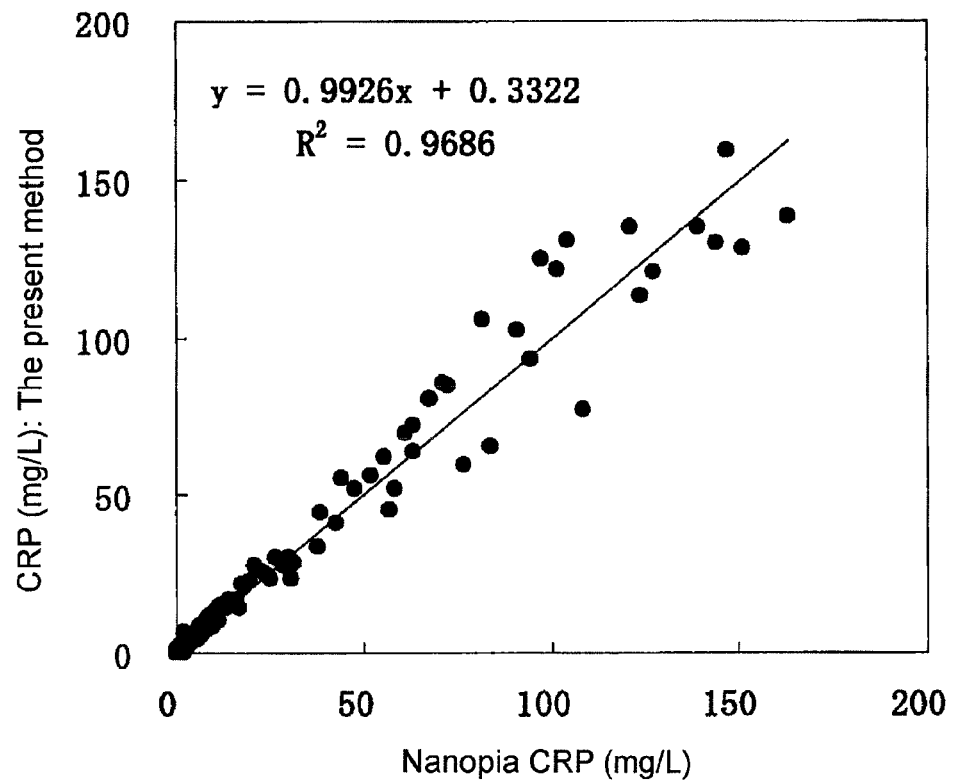
Correlation between commercially available CRP measurement kit (Nanopia CRP) and the present method when HCT correction is performed

[Fig.12]
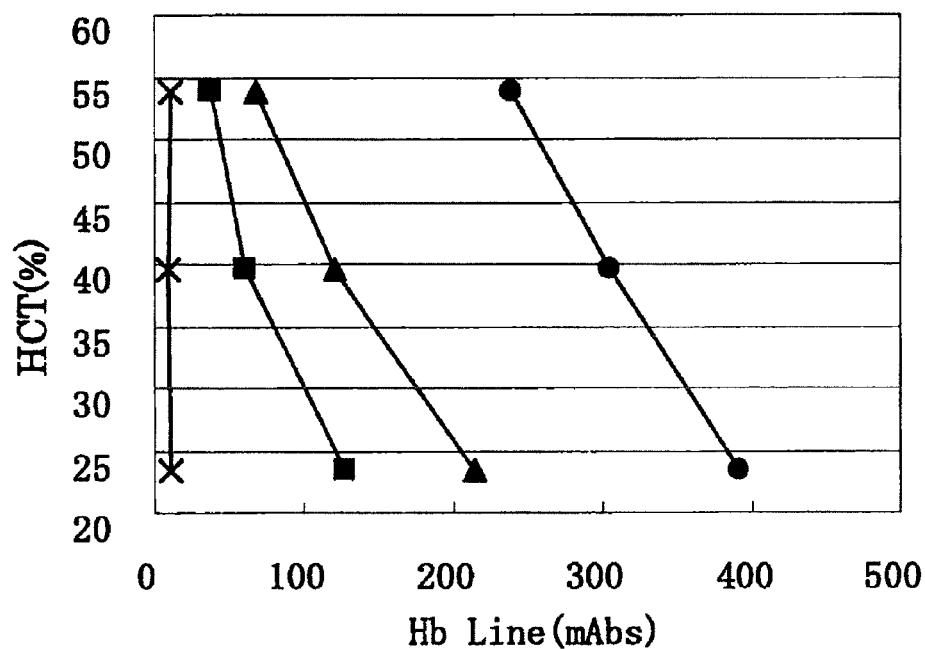
Effect of capillary flow time of membrane on Hb measurement

ASSAY, IMMUNOCHROMATOGRAPHIC TEST STRIP, AND ASSAY REAGENT KIT FOR MEASURING AN ANALYTE, USING A HEMATOCRIT CORRECTION

TECHNICAL FIELD

The present invention relates to a measurement method of measuring an analyte in a sample by immunochromatography, an immunochromatographic test strip for measuring an analyte in a sample by immunochromatography, and a measurement reagent kit for immunochromatography including the immunochromatographic test strip and a diluting solution. The present invention particularly relates to a technique of measuring hemoglobin concentration and the concentration of a second analyte in the same sample derived from blood by using immunochromatography and correcting the measurement value of the second analyte with a hematocrit value obtained from a measurement value of hemoglobin.

BACKGROUND ART

In the medical field, the medical research field etc., certain components in blood (such as serum albumin, immunoglobulin, hepatitis virus, rheumatoid factor, and C-reactive protein) must be measured and various measurement methods have been developed and implemented for this purpose. In frequently used methods among these methods, immunological assay is becoming main stream and, in the immunological assay, blood collected and acquired from a patient or a subject (hereinafter referred to as whole blood) is centrifuged to acquire supernatant (serum or plasma), which is diluted with an appropriate buffer solution, and an antibody that specifically reacts with an analyte is used for detecting the analyte in the serum or plasma. Such assays include a method based on single radial immunodiffusion using a polyclonal antibody, as qualitative testing. Latex agglutination immunoassay and an immunoturbidimetric method are included as representative quantitative testing.

The needs of "wanting to perform various tests during examination of a patient" are recently increasing even in clinics and small hospitals and the tests are increasingly performed as point-of-care testing (POCT) instead of conventional subcontract testing. The representative examples of such POCT reagents include an immunochromatographic lateral flow test strip. Since an operation of separating plasma and serum from blood is cumbersome and requires skill in the POCT field, testing using whole blood is desired. An assay of measuring an analyte in a whole blood sample by using immunochromatography is disclosed as, for example, a method as well as a reagent and a kit using a test strip fitted with a blood cell separation membrane (Patent Document 1). However, when plasma separated by this procedure is directly used for measurement by immunochromatography based on the principle of sandwich-type immune reaction, if the analyte is excessively present, it is problematic that a "hook phenomenon" (also referred to as a "prozone phenomenon") occurs and causes apparent reduction in value although the highly-concentrated analyte is present in the sample. Therefore, whole blood is normally hemolyzed and diluted for measurement so as to remain within a predetermined measurement range. However, in this case, the concentration of the analyte is diluted by the blood cell volume and the measurement value is lowered as compared to the case of serum or plasma samples and, therefore, the measurement value must be corrected by using a hematocrit value (volume percent of red cell). The correction of the measurement value of an analyte using a hematocrit value (volume percent of red cell) will hereinafter also simply be referred to as hematocrit correction.

The problem of the apparent reduction in value is normally corrected by performing uniform multiplication by a correction coefficient acquired from an average hematocrit value of healthy individuals. However, the hematocrit value varies among individuals and the reference value thereof ranges from 39 to 52% in men and 35 to 48% in women. Therefore, an accurate analyte concentration cannot be acquired by the correction using multiplication by a uniform coefficient. Therefore, to perform accurate hematocrit correction, the correction must be performed with a hematocrit value separately measured by using the same sample used for measuring the analyte concentration.

The hematocrit value is conventionally obtained by a microhematocrit method based on a centrifuging method or by using an automated hemocytometer through calculations from the number of red blood cells and an average red blood cell volume. On the other hand, another method using conversion from a measurement result of whole blood into a measurement value in the case of measuring serum or plasma is reported as a method of converting blood measurement result and, in this method, a hemoglobin concentration (g/L) in whole blood is measured; a numerical value obtained by multiplying the acquired hemoglobin concentration by about $3/10$ is adopted as a hematocrit value (%); and the hematocrit value is used for converting a measurement result from whole blood into a measurement value in the case of measuring serum or plasma (Patent Document 2). However, since the hemoglobin concentration and the hematocrit value must be obtained by a method different from an immunochromatographic assay, this method is cumbersome, requires time and cost, and therefore cannot satisfy needs of testing in the POCT field.

Therefore, a method of measuring an analyte and hemoglobin at the same time based on immunochromatography is desired; however, since the hemoglobin concentration in whole blood is normally several dozen g/L to 200 g/L, which is very high concentration, 10,000- to 100,000-times dilution is required for an assay based on the principle of a normal sandwich-type immunoassay. In this method, a large amount of a diluting solution is required for performing the dilution at one step, leading to deterioration of measurement accuracy. A method using multistep dilution problematically lacks practicality for a testing method in the POCT field. To solve these problems, desired is an immunochromatographic assay that is capable of measurement, with a hemolytic dilution operation of whole blood by a factor of at most 50 to 400.

CITATION LIST

Patent Literature

Patent Document 1: Published PCT Application WO 2010/001598
Patent Document 2: Japanese Laid-Open Patent Publication No. 2001-272403

SUMMARY OF INVENTION

Technical Problem

For example, a blood concentration of C-reactive protein (hereinafter also referred to as "CRP") is equal to or less than 3 mg/L in healthy individuals, at most about 35 mg/L after the operation or in the case of acute bacterial infection, and up to about 1000 mg/L in severely injured individuals. On the other hand, a blood concentration of hemoglobin is normally several dozen g/L to 200 g/L, which is different in concentration by a factor of about 50 to 67000 from CRP, and is very high concentration for an analyte subjected to an immunoassay. Therefore, when it is attempted to measure the both of CRP and hemoglobin in an assay based on the principle of sandwich-type immunochromatography, the dilution rate of a sample must considerably be changed depending on the analyte and, therefore, measurement in the same sample (sample at the same dilution rate) is very difficult.

The greatest factors prescribing a measurement range of an immunoassay include avidity between antigen and antibody and various environmental factors affecting the binding reaction thereof. These environmental factors include temperature, time, pH, ion environment, and addition of agents producing certain effects such as surfactants and reaction accelerators. The measurement of the concentrations of CRP and hemoglobin at the same time in the same sample can be enabled in principle by selecting antibodies having different avidities and achieving appropriate environmental factors such that the significant concentration gap is filled. However, it is not easy to prepare such a combination of antibodies and to achieve the appropriate environmental factors.

In fact, when the present inventors initially considered the simultaneous measurement of CRP and hemoglobin by sandwich type immunochromatography, 50- to 200-fold dilution was sufficient for measuring CRP, while 2000- to 100.000-fold dilution was required for measuring hemoglobin. Therefore, it has been unable to measure CRP and hemoglobin by using the same diluted sample.

An object of the present invention is to provide a method of measuring concentrations of an analyte and hemoglobin in the same sample by immunochromatography by using the same diluted sample and a method of performing hematocrit correction of a measurement value of the analyte by using a measurement value of hemoglobin and to provide a test strip and a reagent kit for immunochromatography used in these methods.

Solution to Problem

The present inventors have found that the quantity of hemoglobin can be determined by an immunochromatographic test strip by utilizing a phenomenon in which the intensity of reflected light is reduced, with increasing concentration of hemoglobin, in colloidal gold label captured by a line of anti-hemoglobin antibody immobilized on an insoluble membrane support of the immunochromatographic test strip, even in a sample obtained by diluting and hemolyzing blood by a facer of about 100, i.e., even within the range of hemoglobin concentrations in the sample equal to or greater than the concentration at which the maximum signal value of hemoglobin measurement is obtained (hereinafter also referred to as a prozone phenomenon region), and that CRP can be measured in the diluted sample, leading to the completion of the present invention.

The "immunochromatographic test strip (test strip for immunochromatography)" refers to those including at least an insoluble membrane support necessary for immunochromatography and further including a reagent component, another membrane, etc., as needed.

The present invention comprises the following.

(1) A method of measuring a sample containing at least the first analyte by immunochromatography including the following step A, wherein the concentration of the first analyte in the sample is measured in the range of concentrations equal to or greater than the concentration at which the maximum signal value of the first analyte is acquired (prozone phenomenon region), A. the step of measuring the first analyte in the sample by competitive immunochromatography using 1) and 2) described below:

1) a conjugate in which a first antibody against the first analyte is immobilized to a label; and 2) an insoluble membrane support to which a second antibody against the first analyte is immobilized (if an epitope of the first antibody against the first analyte is monovalent, an epitope of the second antibody is different from the first antibody, while if an epitope of the first antibody is multivalent, an epitope of the second antibody may be the same as the first antibody or the first antibody may be the same as the second antibody in some cases).

(2) The method of (1), wherein step A further uses 3) and 4) described below and wherein the conjugate of 1) is contained in a pad to form a conjugate pad and disposed on the upstream side of the insoluble membrane support of 2), 3) a sample pad located on the upstream side of the conjugate pad and supplied with a sample, and 4) an absorbent pad located on the downstream side of the insoluble membrane support of 2).

(3) The method of (1) or (2), wherein the first analyte is hemoglobin, and wherein the sample is obtained by diluting and hemolyzing blood into the range of concentrations equal to or greater than the range of concentrations at which the maximum signal value of hemoglobin measurement is acquired (prozone phenomenon region).

(4) A method of measuring a sample containing at least hemoglobin, which is the first analyte, and the second analyte by immunochromatography including the following steps A to D:

A. the step of measuring the first analyte in the sample by competitive immunochromatography using 1) and 2) described below, 1) a conjugate in which a first antibody against the first analyte is immobilized to a label, and 2) an insoluble membrane support to which a second antibody against the first analyte is immobilized (if an epitope of the first antibody against the first analyte is monovalent, an epitope of the second antibody is different from the first antibody, while if an epitope of the first antibody is multivalent, an epitope of the second antibody may be the same as the first antibody or the first antibody may be the same as the second antibody in some cases);

B. the step of measuring the second analyte in the sample by immunochromatography using 5) and 6) described below, 5) a conjugate in which a first antibody against the second analyte is immobilized to a label, and 6) an insoluble membrane support to which a second antibody against the second analyte is immobilized (if an epitope of the first antibody against the second analyte is monovalent, an epitope of the second antibody is different from the first antibody, while if an epitope of the first antibody is multivalent, an epitope of the second antibody may be the same as the first antibody or the first antibody may be the same as the second antibody in some cases);

C. the step of obtaining the hematocrit value of the sample from the measurement value of the first analyte acquired at step A; and D. the step of correcting the measurement value of the second analyte acquired at step B by using the hematocrit value acquired at step C.

(5) The method of (4), wherein steps A and B are steps using the same insoluble membrane support.

(6) The method of (5), wherein steps A and B are performed in the same flow passage.

(7) The method of any one of (4) to (6), wherein the second analyte is CRP.

(8) An immunochromatographic test strip for measuring a sample containing at least the first analyte and the second analyte by immunochromatography, said immunochromatographic test strip comprising the following E and F:

E. a test strip for measuring the first analyte including 1) and 2) described below, 1) a conjugate in which a first antibody against the first analyte is immobilized to a label, and 2) an insoluble membrane support to which a second antibody against the first analyte is immobilized (if an epitope of the first antibody against the first analyte is monovalent, an epitope of the second antibody is different from the first antibody, while if an epitope of the first antibody is multivalent, an epitope of the second antibody may be the same as the first antibody or the first antibody may be the same as the second antibody in some cases); and F. a test strip for measuring the second analyte including 5) and 6) described below, 5) a conjugate in which a first antibody against the second analyte is immobilized to a label, and 6) an insoluble membrane support to which a second antibody against the second analyte is immobilized (if an epitope of the first antibody against the second analyte is monovalent, an epitope of the second antibody is different from the first antibody, while if an epitope of the first antibody is multivalent, an epitope of the second antibody may be the same as the first antibody or the first antibody may be the same as the second antibody in some cases).

(9) The immunochromatographic test strip of (8), wherein the conjugates of 1) of E and 5) of F are contained in the same pad to form a conjugate pad, and wherein the insoluble membrane support of 2) of E is the same as the insoluble membrane support of 5) of F.

(10) The immunochromatographic test strip of (9), wherein E and F are disposed in the same flow passage.

(11) The immunochromatographic test strip of any one of (8) to (10), further comprising the following G and H, wherein the conjugates of 1) of E and 5) of F are contained in a pad to form a conjugate pad and disposed on the upstream side of the insoluble membrane support of 2) of E and 6) of F, G. a sample pad located on the upstream side of the conjugate pad and supplied with a sample, and H. an absorbent pad located on the downstream side of the insoluble membrane support of 2) of E and 6) of F.

(12) The immunochromatographic test strip of any one of (8) to (11), wherein the first analyte is hemoglobin.

(13) The immunochromatographic test strip of (12), wherein the second analyte is CRP.

(14) An assay reagent kit for immunochromatography comprising: the immunochromatographic test strip of (12) or (13); and a diluting solution for hemolysis and dilution of hemoglobin.

(15) A method of measuring a sample containing at least the first analyte and the second analyte by immunochromatography including the following steps A and B:

A. the step of measuring the first analyte in the sample by competitive immunochromatography using 1) and 2) described below, 1) a conjugate in which a first antibody against the first analyte is immobilized to a label, and 2) an insoluble membrane support to which a second antibody against the first analyte is immobilized (if an epitope of the first antibody against the first analyte is monovalent, an epitope of the second antibody is different from the first antibody, while if an epitope of the first antibody is multivalent, an epitope of the second antibody may be the same as the first antibody or the first antibody may be the same as the second antibody in some cases); and B. the step of measuring the second analyte in the sample by immunochromatography using 5) and 6) described below, 5) a conjugate in which a first antibody against the second analyte is immobilized to a label, and 6) an insoluble membrane support to which a second antibody against the second analyte is immobilized (if an epitope of the first antibody against the second analyte is monovalent, an epitope of the second antibody is different from the first antibody, while if an epitope of the first antibody is multivalent, an epitope of the second antibody may be the same as the first antibody or the first antibody may be the same as the second antibody in some cases).

(16) The method of (15), wherein the second analyte is CRP.

For a reason that the measurement is enabled in the prozone phenomenon region conventionally considered to be unsuitable for quantification, the present inventors have presumed as follows. The hemoglobin concentration is too high in a blood sample diluted and hemolyzed by a factor of about 100, resulting in free hemoglobin unable to bind with anti-hemoglobin antibody-immobilized colloidal gold (conjugate). Thus, the phenomenon as described above occurs since the free hemoglobin competes with a complex of anti-hemoglobin antibody-immobilized colloidal gold and hemoglobin when binding to the anti-hemoglobin antibody immobilized on the insoluble membrane support.

Advantageous Effects of Invention

According to the present invention, even in a sample containing a highly-concentrated analyte, the concentration of the analyte can be measured within the range of concentrations equal to or greater than the concentration at which the maximum signal value can be acquired (prozone phenomenon region) in the measurement system of the analyte, thereby considerably reducing the effort and cost required for diluting the sample.

The application of the present invention to the measurement of hemoglobin enables the provision of an immunochromatographic test strip and an assay reagent kit for immunochromatography capable of measuring the concentrations of an analyte and hemoglobin in the same sample by the same immunochromatography and performing the hematocrit correction of the measurement value of the analyte from the measurement value of hemoglobin and, therefore, the accurate blood concentration measurement of the analyte can be performed in a short time with simple operations as compared to the conventional means, thereby meeting the social needs in the POCT field.

BRIEF DESCRIPTION OF DRAWINGS

FIG. 1 shows a schematic structure of an immunochromatographic test strip.

FIG. 2 shows a result of hemoglobin measurement of Example 1.

FIG. 3 shows a calibration curve in CRP measurement of Example 1.

FIG. 4 is a diagram of relationship between the intensity of reflected light from a hemoglobin measurement line and the hematocrit value of Example 1.

FIG. 5 is a diagram of correlation between the CRP concentration acquired by using an immunochromatographic test strip of the present invention without hematocrit correction in Example 1 and the CRP concentration acquired by using a commercially available CRP measurement kit ("Nanopia CRP" manufactured by Sekisui Medical Co., Ltd.).

FIG. 6 is a diagram of correlation between the CRP concentration acquired with hematocrit correction in Example 1 and the CRP concentration acquired by using the commercially available CRP measurement kit ("Nanopia CRP" manufactured by Sekisui Medical Co., Ltd.).

FIG. 7 is a diagram of correlation between the CRP concentration when the CRP concentration acquired by the immunochromatographic test strip of the Example 1 is uniformly corrected with an average hematocrit value of 44% and the CRP concentration acquired by using the commercially available CRP measurement kit ("Nanopia CRP" manufactured by Sekisui Medical Co., Ltd.).

FIG. 8 is a diagram of relationship between the intensity of reflected light from a hemoglobin measurement line and the hematocrit value of Example 2.

FIG. 9 shows a calibration curve in CRP measurement of Example 2.

FIG. 10 is a diagram of correlation between the commercially available CRP measurement kit (Nanopia CRP) and the present method when HCT correction is not performed in Example 2.

FIG. 11 is a diagram of correlation between the commercially available CRP measurement kit (Nanopia CRP) and the present method when HCT correction is performed in Example 2.

FIG. 12 is a diagram of the effect of capillary flow time of a membrane on Hb measurement.

DESCRIPTION OF EMBODIMENTS

Description will be made of a measurement method with hematocrit correction that is one of embodiments of the present invention in detail by taking as an example a measurement method when the second analyte is CRP. In this case, the first analyte is hemoglobin and the second analyte is CRP.

When CRP is measured with the measurement method of the present invention, blood is used as a sample after hemolyzed and diluted to a desired concentration at the same time such that CRP and hemoglobin can simultaneously be measured by an immunoassay based on the principle of immunochromatography.

The hemoglobin concentration in a sample in the measurement method of the present invention must be within the range of concentrations equal to or greater than the concentration at which the maximum signal value of hemoglobin measurement is acquired (prozone phenomenon region). In other words, the hemoglobin concentration in a sample must be set to fall within the range of concentrations equal to or greater than the concentration at which the maximum signal value of hemoglobin measurement is acquired (prozone phenomenon region). Specifically, by changing the factor of dilution as appropriate, a sample is diluted to be within the range equal to or greater than the concentration at which the maximum signal value of hemoglobin measurement is acquired. As a result, the hemoglobin concentration in a sample is set equal to or greater than the concentration at which the maximum signal value of hemoglobin measurement is acquired, and hemoglobin concentration can be obtained from the degree of reduction in a detection intensity inversely proportional to the hemoglobin concentration. A preliminary test can be performed in advance to obtain such a concentration at which the maximum signal value of hemoglobin measurement is acquired. Alternatively, such a concentration can be predicted in advance from a hemoglobin concentration predicted from the type of samples (characteristics of a patient) and a past preliminary test result. Specifically, a sample of blood diluted and hemolyzed by a factor of 50 to 200 can be used for measuring CRP and hemoglobin in the same sample at the same time by immunochromatography. Desirably, it is preferred to set the dilution rate to 100 times since a CRP measurement range will be set to 0.2 to 20 mg/mL.

The measurement of CRP with the measurement method of the present invention includes the steps of dripping the sample of diluted and hemolyzed blood onto a sample pad of an immunochromatographic test strip, measuring the hemoglobin concentration at a measurement part (hereinafter also referred to as a "hemoglobin measurement line") having an anti-hemoglobin antibody, which is an antibody against hemoglobin, (a second antibody to hemoglobin) immobilized to an insoluble membrane support, and obtaining a hematocrit value of the blood sample from the measurement value of hemoglobin. Specifically, the hemoglobin concentration is measured by using a conjugate in which a first antibody to hemoglobin is immobilized to a label and an insoluble membrane support to which the second antibody to hemoglobin is immobilized (if the epitope of the first antibody to hemoglobin is monovalent, the epitope of the second antibody is different from the first antibody, while if the epitope of the first antibody is multivalent, the epitope of the second antibody may be the same as the first antibody or the first antibody may be the same as the second antibody in some cases). The hemoglobin concentration may be obtained directly as a measurement value from the difference in the signal from the hemoglobin measurement line on the insoluble membrane support having the second antibody to hemoglobin immobilized or may be a hemoglobin concentration calculated from the difference in the signal. According to the measurement method of the present invention, since the hemoglobin concentration in the sample is measured within the range of concentrations equal to or greater than the concentration at which the maximum signal value of hemoglobin measurement is acquired (prozone phenomenon region), the hemoglobin concentration is obtained from the degree of reduction in the absorbance or the reflected light intensity inversely proportional to the hemoglobin concentration.

The hematocrit value can be calculated from a correlation expression between the measured difference in the signal or the value of hemoglobin concentration and a hematocrit value provided by an official method such as a centrifugal method.

Although the immunochromatographic test strip may be a test strip for measuring only hemoglobin, it is more desirable if the test strip is a single immunochromatographic test strip produced to enable the simultaneous measurement of CRP and hemoglobin. A desirable form is an immunochromatographic test strip described in (9) or (10) above of the present invention.

The measurement of CRP with the measurement method of the present invention includes the steps of dripping the sample of diluted and hemolyzed blood on a sample pad of the immunochromatographic test strip, and measuring the CRP concentration at a measurement part (hereinafter also referred to as a "CRP measurement line") having an anti-CRP antibody that is an antibody to CRP (a second antibody to CRP) immobilized to an insoluble membrane support. Specifically, the CRP concentration is measured by using a conjugate in which a first antibody to CRP is immobilized to a label and the insoluble membrane support to which the second antibody to CRP is immobilized (if the epitope of the first antibody to CRP is monovalent, the epitope of the second antibody is different from the first antibody, while if the epitope of the first antibody is multivalent, the epitope of the second antibody may be the same as the first antibody or the first antibody may be the same as the second antibody in some cases). The CRP concentration may be obtained, directly as a measurement value, from the difference in the signal from the CRP measurement line on the insoluble membrane support having the second antibody to CRP immobilized or may be a CRP concentration calculated from the difference in the signal.

The dripping of a sample onto the sample pad of the immunochromatographic test strip may be performed with any procedures capable of dripping a certain amount of the sample like those normally used in the clinical examination field and may be performed with a measuring pipette or a dropper capable of dripping a certain amount of a droplet. The dripping may manually be performed or an automatically operating device may be used.

A method of measuring a signal derived from the label may be implemented in accordance with a known technique and, for example, if the label is colloidal gold, an absorbance or the intensity of reflected light may be measured. The concentrations of CRP and hemoglobin can concurrently be calculated by extrapolating the difference in the absorbance or the intensity of reflected light into a standard curve of a sample having a known concentration.

The measurement of CRP with the measurement method of the present invention includes the steps of correcting the CRP concentration measured in the CRP measurement line with a hematocrit value calculated from the value of hemoglobin measured in the hemoglobin measurement line of the test strip. In the method of calculating CRP through the hematocrit correction, the calculation is made as is the case with correction through a hematocrit value normally obtained with another method as follows.

$$\text{corrected } CRP \text{ measurement value} = \frac{\text{uncorrected } CRP \text{ measurement value}}{(1 - \text{hematocrit value } (\%) \text{ calculated in the present invention}/100)}$$

Since hemoglobin can be measured in a sample hemolyzed and diluted by a factor of 50 to 400 by utilizing the method of measuring a hemoglobin concentration from the degree of reflected light intensity reduced inversely proportional to the hemoglobin concentration, if a coexisting second analyte can be measured at dilution by a factor of 50 to 400, the same sample can be used for measuring hemoglobin and the second analyte by immunochromatography.

The "second analyte" capable of being subjected to the hematocrit correction refers to a component contained in blood (whole blood) that is a substance from which an accurate measurement value cannot be acquired unless the hematocrit correction is performed. Examples of the second analyte include: inflammation-related markers such as C-reactive protein (CRP), IgA, IgG, and IgM; coagulation or fibrinolysis markers such as fibrin degradation products such as D-dimer, soluble fibrin, TAT (thrombin-antithrombin complex), and PIC (plasmin-plasmin inhibitor complex); cardiovascular-related markers such as oxidized LDL and BNP (brain natriuretic peptide); metabolism-related markers such as adiponectin; tumor markers such as CEA (carcinoembryonic antigen), AFP (α-fetoprotein), CA19-9, CA125, and PSA (prostate-specific antigen); infectious disease-related markers such as HBV (hepatitis B virus) and HCV (hepatitis C virus); allergen-specific IgE (immunoglobulin E); hormones; and drugs.

A test strip and an assay reagent kit for immunochromatography having a mechanism of hematocrit correction of the present invention will be described in detail.

(Antibody)

An antibody to an analyte used in the present invention may be any antibody specifically reacting with the analyte, is not limited by a method of manufacturing the antibody, and may be a polyclonal antibody or a monoclonal antibody. For example, if the analyte is human CRP or human hemoglobin, an anti-human CRP antibody or an anti-human hemoglobin antibody may be any antibody specifically reacting with human CRP or human hemoglobin, is not limited by a method of manufacturing the antibody, and may be a polyclonal antibody or a monoclonal antibody. A hybridoma producing antibody can generally be produced by the cell fusion between spleen cells of an animal immunized by human CRP or human hemoglobin and homologous myeloma cells in accordance with the method of Kohler and Milstein (see Nature, Vol. 256, p. 495, 1975).

When antibodies used are monoclonal antibodies, with regard to the relationship between the antibody immobilized to the label (first antibody) and the antibody immobilized to the insoluble membrane support (second antibody), if the epitope of the first antibody is monovalent, the epitope of the second antibody different from the first antibody is used and, if the epitope of the first antibody is multivalent, the epitope of the second antibody may be the same antibody as the first antibody or the first antibody may be the same antibody as the second antibody. When blood diluted and hemolyzed by a factor of about 100 is used as a sample, antibodies are desirably combined such that a CRP concentration can be measured within a range from 2 to 20 mg/L. For example, in a combination of the antibodies to CRP, it is desirable to use a monoclonal antibody produced by the hybridoma of the accession number FERM BP-11344 as the first antibody immobilized to the label and a monoclonal antibody produced by the hybridoma of the accession number FERM BP-11345 as the second antibody immobilized to the insoluble membrane support. Alternatively, it is desirable to use a combination of anti-human CRP monoclonal antibodies #08210 and #08209 acquired from two hybridomas produces by using human CRP etc., as an antigen by the present inventors with a test method described later.

A combination of the antibodies to hemoglobin may be a combination of anti-human hemoglobin monoclonal antibodies #69202 and #69209 acquired from two hybridomas produces by immunizing a mouse with human hemoglobin by the present inventors, for example, or may be an appropriate combination selected as appropriate from commercially available anti-hemoglobin antibodies.

(Sample Pad)

The term "sample pad" used herein refers to a part supplied with a sample and includes any material or shape capable of absorbing a liquid sample in the form of a pad and allowing a liquid component and an analyte in the sample to pass through. Specific examples of materials suitable for the sample pad include, but not limited to, glass fibers, acrylic fibers, hydrophilic polyethylene materials, dry papers, pulp, fabrics, etc. It is preferable to use a glass fiber pad. The sample pad may additionally have the function of a conjugate pad described later. The sample pad may contain a blocking reagent commonly used for preventing or suppressing non-specific reactions (adsorption) in the insoluble membrane support having the antibody immobilized. For the blocking reagent, a reagent having no effect on a reaction system can appropriately be selected from NEO PROTEIN SAVER sericin, ImmunoBlock™, Applie Block, SEA BLOCK™/EIA/WB, Blocking One, BSA, Blocking Peptide Fragment, Starting Block™ (PBS) Blocking Buffer, Smart Block™, and HeteroBlock, for example.

(Label)

Materials normally known as antibody-immobilization carriers in immunochromatography can be used for the label. For example, colloidal gold particles, colloidal platinum particles, color latex particles, and magnetic particles are preferable and the colloidal gold particles are particularly preferable.

The particle size (particle diameter) of colloidal gold particles is known to significantly affect the sensitivity of immunochromatographic test strip and the particle size of colloidal gold particles used in the present invention is preferably 20 to 60 nm and particularly preferably 30 to 45 nm. The colloidal gold particles can be manufactured with a commonly known method, for example, by dripping and stirring a trisodium citrate aqueous solution in a heated tetrachloroaurate (III) aqueous solution.

The case of using the colloidal gold particles will hereinafter be described in detail.

(Conjugate)

In this description, a "conjugate" refers to a label having an immobilized antibody such as an anti-CRP antibody, an anti-hemoglobin antibody, and a control antibody.

(Sensitization of Antibody to Label)

The immobilization of a first antibody to the analyte to the colloidal gold particles, for example, the immobilization of the first antibody to CRP or hemoglobin to the colloidal gold particles, is normally achieved by physisorption. The immobilization by physisorption is performed in a system consisting of a buffer solution, and the antibody concentration is preferably prepared at 1 μg/mL to 5 μg/mL, and the buffer solution and pH are preferably a 2 mmol/L phosphate buffer solution (pH 6 to 7) or a 2 mmol/L borate buffer solution (pH 8 to 9) and more preferably a 2 mmol/L phosphate buffer solution (pH 7.0). The regions on the colloidal gold particles without bound antibody are preferably blocked by binding with bovine serum albumin (BSA) etc. The conjugate which is produced in this way and in which the first antibody is immobilized to the label, such as the colloidal gold particles, is dispersed and preserved in a preservation reagent for inhibiting denaturalization. Proteins such as bovine serum albumin (BSA), glycerin, sugar, etc., are used for this denaturalization inhibiting agent.

(Detection Reagent)

In the present invention, a "detection reagent" is a solution containing at least the conjugate.

The detection reagent may contain, for example, one or more stabilizers, solubilizers, etc., so that the conjugate is maintained in a stable state to facilitate the specific reaction between the antibody immobilized to the conjugate and the analyte such as CRP and hemoglobin or to make the conjugate dissolved and fluidized promptly and effectively when mixed with the sample. The stabilizers, solubilizers, etc., can include bovine serum albumin (BSA), sucrose, casein, and amino acids, for example.

The detection reagent may contain a known sensitizer such as 2-methacryloyloxyethyl phosphorylcholine as needed for improving detection sensitivity.

The detection reagent may contain a chelate agent of $Ca^{2+}$ ions such as EDTA and EGTA.

The term "detection" or "measurement/assay" as used herein must be construed in the broadest sense including verification and/or quantification of the presence of the analyte, for example, CRP or hemoglobin and must not be construed in a limited manner in any sense.

(Conjugate Pad)

The term "conjugate pad" used herein refers to a part including a detection reagent containing the conjugate specifically reacting with the analyte, for example, a detection reagent containing the conjugate in which the antibody specifically reacting with CRP or hemoglobin is immobilized to the label, the part having a function of allowing the conjugate in the detection reagent and the analyte such as CRP and hemoglobin to form a complex when the sample passes through the conjugate pad. The conjugate pad may be placed adjacent to an insoluble membrane support described later by itself or the conjugate pad may be placed in contact with the sample pad so as to accept the sample passing through the sample pad by a capillary flow and then transporting the sample to another pad (hereinafter referred to as a "3rd pad") in contact with a surface not in contact with the sample pad also by a capillary flow. The choice of one or more parts of the conjugate pad and how the chosen parts are placed relative to the insoluble membrane support, the sample pad, the 3rd pad, etc., may be changed as appropriate.

Materials suitable for the conjugate pad include, but not limited to, paper, a cellulose mixture, nitrocellulose, polyester, an acrylonitrile copolymer, glass fibers, and nonwoven fibers such as rayon. It is preferable to use a pad consisting of nonwoven fabric made of glass fiber.

The conjugate pad may contain a "control reagent" to ensure the reliability of the assay, such as a labeled antibody not reactive with analyte components, and a highly antigenic protein such as labeled KLH (keyhole limpet hemocyanin). Such a control reagent is a component (substance) not expected to be present in the sample and is selectable as appropriate. The conjugate pad may contain, for example, one or more stabilizers, solubilizers, etc., so that the detection reagent is maintained in a stable state to facilitate the specific reaction with the analyte such as CRP and hemoglobin or to make the conjugate dissolved and fluidized promptly and effectively when the conjugate contacts with the sample. The stabilizers, solubilizers, etc., can include bovine serum albumin (BSA), sucrose, casein, and amino acids, for example. In particular, an anti-CRP antibody may have considerably different reactivity in the presence and absence of $Ca^{2+}$ ions and the conjugate pad may contain a chelate agent of $Ca^{2+}$ ions such as EDTA and EGTA as appropriate so as to control the reactivity or, conversely, calcium salts such as $CaCl_2$ may be added so as to add $Ca^{2+}$ ions.

(3rd Pad)

In the present invention, the 3rd pad can be placed so as to remove components unnecessary for the measurement of the analyte (e.g., CRP or hemoglobin) out of the components present in the sample or the detection reagent so that components necessary for the measurement can smoothly progress in the insoluble membrane support. For example, blood cells, insoluble blood cell fractures, etc., present in hemolyzed blood sample are desirably removed as the components unnecessary for the measurement of CRP and hemoglobin. The 3rd pad may also be given an additional effect of preliminarily removing agglutinations, among those generated by an antigen-antibody reaction, growing to a size unable to move to and flow smoothly in the insoluble membrane support. The 3rd pad may comprise any material or shape allowing the passage of the liquid component and the analyte in the sample. Examples of the 3rd pad include, but not limited to, pads made of glass fibers, acrylic fibers, hydrophilic polyethylene materials, dry papers, pulp, fabrics, etc. It is preferable to use a blood cell separation membrane or a similar membrane.

(Insoluble Membrane Support)

In the present invention, the insoluble membrane support (hereinafter also simply referred to as the membrane) may be a conventionally known support and may be made of any material. The materials of the membrane include, but not limited to, polyethylene, polyethylene terephthalate, nylons, glass, polysaccharide such as cellulose and cellulose derivatives, or ceramics. Specific examples include glass fiber filter paper and cellulose filter paper available from Millipore, Toyo Roshi, and Whatman.

On the insoluble membrane support, the second antibody to the analyte is immobilized to a part (measurement line) of measuring the analyte.

Appropriate selection of a pore diameter, configuration, etc., of the insoluble membrane support can control the speed of an immune complex of the conjugate in which the first antibody (e.g., an anti-CRP antibody) is immobilized to the label such as colloidal gold particles and the analyte (e.g., CRP) flowing through the membrane. The amount of labeled antibody binding to a second antibody against the analyte immobilized to the membrane can be adjusted by controlling the speed of the immune complex flowing through the membrane. Thus, the pore diameter and configuration of the membrane are desirably optimized by considering the compatibility with the other constituent materials of the immunochromatographic test strip of the present invention. Particularly when the analyte is the first analyte such as hemoglobin present in the sample at higher concentration, hemoglobin is measured by utilizing a competitive reaction between hemoglobin not binding the conjugate and the immune complex of hemoglobin and the conjugate, the capillary flow time in this hemoglobin measurement is preferably 30 seconds/cm to 60 seconds/cm as in the examples described later. It is preferable to use HiFlow Plus SHF180 manufactured by Millipore etc.

(Immobilization of Antibody to Insoluble Membrane Support)

A known method can be employed as a method of immobilizing a second antibody to the analyte (e.g., CRP or hemoglobin) to the insoluble membrane support. For example, if an immunochromatographic test strip is of a flow-through format (flow through-based), a second antibody is prepared as a solution at a predetermined concentration and a certain amount of the solution is applied to the insoluble membrane support at a point or in a shape of a certain symbol such as "+". If an immunochromatographic test strip is of a lateral-flow format (lateral flow-based), a second antibody is prepared as a solution at a predetermined concentration and the solution is applied to the insoluble membrane support in a line shape by using a device having a mechanism capable of horizontally moving while discharging the solution from a nozzle at a constant rate. In this case, the concentration of the second antibody in the solution is preferably 0.1 mg/mL to 5 mg/mL and more preferably 0.5 mg/mL to 2 mg/mL. An immobilized amount of the second antibody on the insoluble membrane support can be optimized by adjusting an amount of the solution dripped onto the insoluble membrane support if the immunochromatographic test strip is of the flow-through format, and can be optimized by adjusting a discharge rate of the solution from the nozzle of the device if the immunochromatographic test strip is of the lateral-flow format. Particularly in the case of the lateral-flow format, the discharge rate is preferably 0.5 µL/cm to 2 µL/cm. The term "flow-through format (flow through-based)" as used herein refers to a format in which the sample etc., perpendicularly pass through the insoluble membrane support for flow progression and the term "lateral-flow format (lateral flow-based)" refers to a format in which the sample etc., move in parallel with the insoluble membrane support for flow progression.

In the case of the lateral-flow format, the position of application of a second antibody to an analyte (e.g., CRP or hemoglobin) to the insoluble membrane support may be placed such that the analyte, the immune complex in which the analyte is bound to the conjugate, etc., progress from the conjugate pad by capillary action and sequentially pass through the measurement sites (measurement lines) with each of the second antibodies applied. For example, if the analytes are CRP and hemoglobin in a blood sample, the arrangement is preferably made such that a CRP measurement line with an anti-CRP antibody applied is located upstream while a hemoglobin measurement line with an anti-hemoglobin antibody applied is located downstream. In this case, it is desirable to keep a sufficient distance between the respective measurement lines such that the signal of a label can be detected. In the case of the flow-through format, the position of application of the second antibody to CRP or hemoglobin may also be placed such that the signal of a label can be detected.

An antibody solution applied to the insoluble membrane support can normally be prepared by using a predetermined buffer solution. The types of the buffer solution may include commonly used buffer solutions such as phosphate buffer solution, Tris buffer solution, and Good's buffer solution. The buffer solution preferably has pH in a range of 6.0 to 9.5, more preferably 6.5 to 8.5, further preferably 7.0 to 8.0. The buffer solution may contain salts such as NaCl, stabilizer and antiseptic such as sucrose, and a preservative such as ProClin. The salts include those added for adjusting ionic strength, such as NaCl, as well as those added at the step of adjusting pH of the buffer solution, such as sodium hydroxide.

After the second antibody is immobilized to the insoluble membrane support, the blocking can be performed by using a commonly used blocking agent in a solution or vapor state with a cover for the portion other than the part having the second antibody immobilized. In this description, an insoluble membrane support having an antibody immobilized as described above is also referred to as an "antibody-immobilized membrane".

(Absorbent Pad)

The term "absorbent pad" used herein refers to a liquid-absorbing part absorbing the sample that has migrated/passed through the insoluble membrane support to control the flow progression of the sample. In a lateral-flow format, the absorbent pad may be provided on the downstream end of the immunochromatographic test strip, and in a flow-through format, the absorbent pad may be provided beneath the antibody immobilized membrane, for example.

Examples of the absorbent pad include, but are not limited to, filter paper. It is preferable to use 740-E manufactured by Whatman etc.

(Immunochromatographic Test Strip)

In the present invention, a "immunochromatographic test strip" (hereinafter also referred to as the "test strip") shall be a product including at least an insoluble membrane support having an antibody immobilized and shall be a product containing a reagent component as needed or a product appropriately disposed and fitted with other membranes etc. Other membranes may be a sample pad, a conjugate pad, an absorbent pad, etc. The test strip is usually formed on a solid phase support such as an adhesive plastic sheet. The solid phase support, as well as the adhesive component, should be made of a material that does not hinder the capillary flow of the sample. Lamination with a polyester film etc., can be performed for the purpose of increasing the mechanical strength of the antibody immobilized membrane and preventing evaporation (drying) of water during the assay. The test strip may be used after being stored in or mounted on a container (housing) appropriate with respect to the size of the test strip, the manner and position of application of the sample, the immobilization position of antibody on the antibody-immobilized membrane, the signal detection method, etc., and such a stored/mounted state is referred to as a "device".

(Same Test Strip)

The test strip for measuring the first analyte such as hemoglobin may be the same test strip as, or a separate test strip different from, the test strip for measuring the second analyte such as CRP. Therefore, in the case of the same test strip, the test strip is made up of the same conjugate pad containing a conjugate in which a first antibody against the first analyte is immobilized to a label and a conjugate in which a first antibody against the second analyte is immobilized to a label, and the same insoluble membrane support having a second antibody against the first analyte and a second antibody against the second analyte are immobilized, as described above. However, if different separate test strips are used, the same sample is measured by using a test strip for measuring the first analyte made up of a conjugate pad containing a conjugate in which a first antibody against the first analyte is immobilized to a label and an insoluble membrane support having a second antibody against the first analyte immobilized, and a test strip for measuring the second analyte made up of a conjugate pad containing a conjugate in which a first antibody against the second analyte is immobilized to a label and an insoluble membrane support having the second antibody against the second analyte immobilized. When the same test strip is used, the size can be reduced and the measurement can easily be performed. On the other hand, when separate test strips are used, a combination with a plurality of other analytes can be made whenever necessary and the individual test strips are thought to be more generally and frequently used. Even when the test strips are separated, the test strips can obviously be housed in the same housing to form one device.

The immunochromatographic test strip of the present invention is preferably used for measuring C-reactive protein (CRP) (hereinafter also referred to as a "immunochromatographic CRP assay test strip (immunochromatographic test strip for CRP assay)"). The immunochromatographic CRP assay test strip may be a test strip including at least a membrane having an anti-CRP monoclonal antibody and an anti-hemoglobin antibody immobilized as well as a conjugate in which an anti-CRP monoclonal antibody is immobilized to a label and a conjugate in which an anti-hemoglobin antibody immobilized to a label, and may contain another reagent or constituent element depending on the measurement condition and the sample.

In this description, the "insoluble membrane support" is also referred to as a "solid phase" and, allowing, or a state of allowing, the insoluble membrane support to physically or chemically support an antigen or an antibody may be expressed as "immobilize/immobilizing", "immobilized/immobilization", "solid-phased", "sensitize/sensitization", or "adsorp/adsorption".

(Sample)

The "sample" to be measured in the measurement method of the present invention is blood (whole blood or hemolyzed whole blood).

(Diluting Solution)

The diluting solution used in the present invention has an effect of sufficiently hemolyzing red blood cells in a short time. The diluting solution of any composition may be used as long as the antigen-antibody reaction is not significantly inhibited or, conversely, not significantly facilitated in a measurement system of the second analyte such as hemoglobin and CRP causing a defect of flow progression by capillary action due to excessive agglutination, or the signal detection of antigen-antibody reaction depending on the concentration of antigen is not disabled. The diluting solution having such an effect may be purified water or a buffer solution having pH 6.0 to 10.0, for example. The buffer solution may preferably be a 10 to 20 mmol/L buffer solution, for example, 10 to 20 mmol/L phosphate buffer solution, 10 to 20 mmol/L Tris-HCl buffer solution, or 10 to 20 mmol/L glycine-HCl buffer solution. A surfactant can be added to these diluting solutions so as to increase the hemolytic effect and control the flow progression rate of the sample etc., in the membrane. Particularly, in the system of measuring CRP that is an example of the second analyte, if the monoclonal antibody produced by the hybridoma of the accession number FERM BP-11344 is used as the first antibody immobilized to the label and the monoclonal antibody produced by the hybridoma of the accession number FERM BP-11345 is used as the second antibody immobilized to the insoluble membrane support, the diluting solution can contain sodium alkylsulfate expressed by a general formula $CH_3(CH_2)_nOSO_3Na$ (n=5 to 10) to adjust the measurement range. It is desirable to add 0.05 to 0.3% of sodium hexylsulfate, sodium octylsulfate, etc., to the diluting solution since a preferable concentration reaction curve is acquired. In this case, a desirable dilution rate is 50 to 200 times. The diluting solution may contain a chelate agent of $Ca^{2+}$ ions such as EDTA and EGTA.

EXAMPLES

The present invention will specifically be described by giving examples of measuring hemoglobin (hereinafter also referred to as "Hb") as the first analyte and CRP as the second analyte; however, the scope of the present invention is not limited to these examples.

Example 1

1) Production of anti-CRP antibody-sensitized conjugate (conjugate in which an anti-CRP monoclonal antibody is immobilized to colloidal gold particles) and anti-hemoglobin antibody-sensitized conjugate (conjugate in which an anti-hemoglobin monoclonal antibody is immobilized to colloidal gold particles)

The anti-CRP monoclonal antibody (Clone: FERM BP-11344) and the anti-hemoglobin monoclonal antibody (Clone: #69202) were prepared to have the following buffer solution conditions and antibody concentrations; 1 mL of each solution was added to 20 mL of a 1 OD/ml colloidal gold particle solution (particle size: 40 nm); and the mixtures were stirred at room temperature for 10 minutes. After the addition of 2 ml of a 10% bovine serum albumin (BSA) aqueous solution to each of the colloidal gold particle-antibody mixtures, the mixtures were further stirred for 5 minutes, and centrifuged at 10,000 rpm at 10 degrees C. for 45 minutes to obtain sediments (the anti-CRP antibody-sensitized conjugate and the anti-hemoglobin antibody-sensitized conjugate). To each of the acquired conjugates, 1.2 mL of Conjugate Dilution Buffer (manufactured by Scripps) was added to suspend the conjugates. The absorbance of each of the conjugates was measured at the maximum absorption wavelength.

i) FERM BP-11344 (20 µg/mL), 2 mmol/L phosphate buffer solution pH 7.0 ii) #69202 (80 µg/mL), 2 mmol/L borate buffer solution pH 9.0

2) Production of conjugate pad

A conjugate solution was prepared by mixing the anti-CRP antibody-sensitized conjugate and the anti-hemoglobin antibody-sensitized conjugate produced in (1) at 20 OD/ml and 10 OD/ml, respectively, with a 20 mmol/L Tris-HCl buffer solution (pH 7.5) containing 1.33% casein and 4% sucrose. A glass fiber pad having a certain volume (No. 8964 manufactured by Pall Corporation) was impregnated with 1.2 volumes (relative to the volume of the pad) of the conjugate solution. The pad was dried at 70 degrees C. for 30 minutes in a dry oven to obtain a conjugate pad. If an additive such as a sensitizer is added as needed, a necessary amount may be added to the conjugate solution before performing the operation above.

3) Production of insoluble membrane support having anti-CRP antibody and anti-hemoglobin antibody immobilized (antibody immobilized membrane)

The anti-CRP monoclonal antibody (Clone: FERM BP-11345) and the anti-hemoglobin monoclonal antibody (Clone: #69209) were prepared at 1 mg/mL as a 10 mmol/L phosphate buffer solution (pH 7.2) containing 2.5% sucrose to apply the anti-CRP monoclonal antibody onto a nitrocellulose membrane (SHF180 manufactured by Millipore) at a position (CRP measurement line) inner from one edge of the short side and the anti-hemoglobin monoclonal antibody on the outside (Hb measurement line) at an interval of about 5 mm by using an immunochromatography dispenser "XYZ3050" (manufactured by BIO DOT) set to be 0.75 µL/cm in a line shape. The membrane was dried at 70 degrees C. for 45 minutes in a dry oven to obtain an antibody immobilized membrane.

4) Production of sample pad

A glass fiber pad (manufactured by Lydall) cut to have a certain volume was impregnated with 1.15 volumes (relative to the volume of the pad) of a 20 mmol/L Tris-HCl buffer solution (pH 7.2) containing 24 mmol/L NaCl, 0.5% sucrose, and 30 mmol/L ethylenediaminetetraacetic acid. The pad was dried at 70 degrees C. for 45 minutes in a dry oven to obtain a sample pad.

5) Production of test strip

On an adhesive plastic sheet (a), the antibody immobilized membrane (b) produced in 3) was disposed and bonded such that an application portion of the anti-CRP antibody (c) (the CRP measurement line) was located on the upstream portion of the flow progression and followed by an application portion of the anti-hemoglobin antibody (d) (the Hb measurement line), and the 3rd pad (i) consisting of a glass fiber pad was further placed. The conjugate pad (e) produced in 2) was then placed and the sample pad (f) produced in 4) was placed to overlap the conjugate pad while the absorbent pad (g) was placed on the end of the other side. Finally, a polyester film (h) was placed and laminated on the top to cover the antibody immobilized membrane and the absorbent pad. The structure formed by overlapping the constituting elements as described above was cut to produce the immunochromatographic test strip. The test strip was stored in/mounted on a dedicated plastic housing (having a sample supply window formed over the sample pad and a detection window formed over the measurement lines, not depicted in FIG. 1) at the time of an assay to achieve a form of an immunochromatographic test device. FIG. 1 is a schematic of a structure of the immunochromatographic test strip.

6) Hemoglobin measurement by competitive immunochromatography utilizing Competitive Reaction (Measurement of Hemoglobin in a Prozone Phenomenon Region)

From one healthy individual agreed to blood collection, 5 mL of blood was collected by using an EDTA-2Na vacuum blood collection tube. A hematocrit value measured by using a portion of the blood with the microhematocrit method was 46% and it was confirmed that the sample is within a reference value. The blood sample was hemolyzed and diluted with a 0.1% sodium hexylsulfate and 10 mmol/L phosphate buffer solution (pH 7.2) by a factor of 50 to 400, and 120 µL of each of the samples was dripped to the sample supply window of the immunochromatographic test device produced in 5) above to measure the reflected light intensity of the Hb measurement line from the detection window of the immunochromatographic test device after five minutes by using an immunochromatography reader ICA-1000 (manufactured by Hamamatsu Photonics K.K.). As a result, as depicted in FIG. 2, a decreasing dose-response curve was obtained indicating that the increase in the hemoglobin concentration causes the reduction in the reflected light intensity of the colloidal gold particles captured by the Hb measurement line having the anti-hemoglobin antibody immobilized on the immunochromatographic test strip.

7) Production of calibration curve of CRP measurement

CRP calibrator A for Nanopia (manufactured by Sekisui Medical Co., Ltd.) was diluted with a 0.1% sodium hexylsulfate and 10 mmol/L phosphate buffer solution (pH 7.2) by a factor of 100, and 120 µL of the sample was dripped to the sample supply window of the immunochromatographic test device produced in 5) to measure the reflected light intensity of the CRP measurement line from the detection window of the immunochromatographic test device after five minutes by using the immunochromatography reader ICA-1000 (manufactured by Hamamatsu Photonics K.K.). FIG. 3 depicts a calibration curve in a range of CRP concentrations from 1.5 to 420 mg/L.

8) Measurement of hematocrit value with microhematocrit method

From 22 healthy individuals agreed to blood collection, twenty two (22) 5-mL blood specimens were collected by using EDTA-2Na vacuum blood collection tubes. A portion of each of the blood specimens was collected by a hematocrit capillary tube (CEN02-0019 manufactured by Drummond) and after sealing the bottom of the capillary tube with dedicated pate (CRITOSEAL, A422 manufactured by HELIX), the capillary tube was centrifuged by a hematocrit centrifuge (H-1200F manufactured by KOKUSAN) at room temperature at 12000 rpm for 10 minutes to measure a hematocrit value by using a measurement panel associated with the centrifuge.

9) Calculation of CRP and hematocrit value using the immunochromatographic test strip of the present invention The CRP concentration and hemoglobin concentration of the 22 blood specimens were measured by using the immunochromatographic test device produced in 5). Specifically, 2 µL of each of the blood specimens was diluted and hemolyzed with a 0.1% sodium hexylsulfate and 10 mmol/L phosphate buffer solution (pH 7.2) by a factor of 100, and 120 µL of the sample was dripped to the sample supply window of the immunochromatographic test device to measure the reflected light intensities of the CRP measurement line and the Hb measurement line from the detection window of the immunochromatographic test device after five minutes by using the immunochromatography reader ICA-1000 (manufactured by Hamamatsu Photonics K.K.). The reflected light intensity of the CRP measurement line was extrapolated to the calibration curve of FIG. 3 to obtain the CRP concentration. FIG. 4 depicts a correlation expression between the reflected light intensity of the Hb measurement line and the hematocrit value acquired in 8). This correlation expression was used for calculating a hematocrit value from the reflected light intensity of the Hb measurement line of each of the blood specimens.

Hematocrit value (%) (calculated value)=(−0.0788)×(reflected light intensity of the Hb measurement line)+68.585

10) Hematocrit correction by the present invention

The CRP measurement value of each of the blood specimens calculated in 9) was subjected to the hematocrit correction by the hematocrit value calculated in 9) in accordance with the following equation.

$$\text{corrected } CRP \text{ measurement value} = \frac{\text{uncorrected } CRP \text{ measurement value}}{(1 - \text{calculated hematocrit value (\%)}/100)}$$

11) Verification of effect of hematocrit correction of the present invention

The CRP concentrations in plasma of the 22 blood specimens were measured by using a commercially available kit based on the measurement principle of a latex agglutination reaction ("Nanopia CRP" manufactured by Sekisui Medical Co., Ltd.). FIG. 5 depicts correlation between the "CRP measurement value" of Nanopia CRP and the CRP concentration calculated in 9), i.e., "CRP measurement value (without HCT correction)". FIG. 6 depicts correlation between the "CRP measurement value" of Nanopia CRP and the hematocrit-corrected CRP concentration calculated in 10), i.e., "CRP measurement value (with HCT correction, the present invention)". FIG. 7 depicts correlation between the "CRP measurement value" of Nanopia CRP and the CRP concentration acquired by uniformly correcting the CRP concentration calculated in 9) with an average hematocrit value (44%), i.e., "CRP measurement value (with uniform correction)".

In the case of the "CRP measurement value (without HCT correction)" not subjected to the hematocrit correction, a slope of a correlation regression equation relative to the CRP measurement value measured by the commercially available CRP measurement kit was about 0.73 and $R^2$ was about 0.965 (FIG. 5) while in the case of the "CRP measurement value (with HCT correction)" subjected to the hematocrit correction of the present invention, the slope was about 1.20 and $R^2$ was about 0.989, and the improvement in correlation with the CRP measurement value measured in the latex agglutination reaction was recognized (FIG. 6).

On the other hand, in the case of the "CRP measurement value (with uniform correction)" acquired by uniform correction with the average hematocrit value, the slope of the correlation regression equation was increased from about 0.73 to 1.30 and, therefore, the y-intercept was changed from about −0.23 to about −0.41, departing from zero (FIG. 7).

From these results, it was demonstrated that the CRP measurement can more accurately be performed by measuring the concentrations of CRP and hemoglobin in the same sample by using the immunochromatographic test strip of the present invention, and by performing the hematocrit correction of the CRP measurement value by utilizing the correlation relationship between the measurement value of hemoglobin and the hematocrit value in the sample.

Test Example 1

Production Method of Anti-Human CRP Monoclonal Antibody

A combination of monoclonal antibodies other than the anti-human CRP monoclonal antibody used in Example 1 was acquired with the following method and was used in Examples 2 and 3.

1) Preparation method of immunizing antigen

After human CRP (manufactured by Radioimmunoassay) was mixed at 1:1 with complete Freund's adjuvant (manufactured by Gibco), emulsion was produced by using a connected syringe and used as an immunizing antigen. Hb was purified by cation exchange chromatography from hemolyzed blood of a red blood cell fraction of blood collected from volunteer. After this purified Hb was mixed at 1:1 with complete Freund's adjuvant in the same way, emulsion was produced and used as an immunizing antigen.

2) Immunization and production method of hybridoma

The immunizing antigen was injected into the abdominal cavity of BALB/c mice (50 to 100 µg per mouse). This operation (immunization) was repeated twice every two weeks. When five weeks had elapsed after the start of immunization, the spleen was extracted from mice with a higher antibody value confirmed by test blood collection and the cell fusion was performed by using 50%-PEG1450 (manufactured by Sigma) with a common procedure. SP2/O was used for myeloma cells. The acquired fused cells were suspended at $2.5 \times 10^6$ cells/mL (as spleen cells) in RPMI1640 medium including HAT, 15% fetal bovine serum, and 10% BM-Condimed H1 Hybridoma Cloning Supplement (Manufactured by Roche) and were dispensed onto 96-well culture plate at 0.2 mL/well. The cells were incubated at 37 degrees C. in a 5% $CO_2$ incubator.

3) Screening of monoclonal antibody producing hybridomas

After 7 to 10 days from the cell fusion, antigen solid-phase ELISA was performed by using the culture supernatant in accordance with a common procedure ("Yaku ni tatsu men-eki jikkenho" published by Kodansha, 1984) to select wells highly reactive with each antigen as positive wells. The cells in the positive wells are subcultured by a 24-well plate.

4) Cloning and monoclonal antibody collection

The hybridomas selected by the screening were cloned by a limiting dilution method to acquire respective hybridomas. To collect the monoclonal antibodies produced by the hybridomas, the hybridomas were administered at an amount of 0.4 to $1.3 \times 10^6$ cells into the abdominal cavity of eight-week old male BALB/c mice subjected to the injection of 0.5 mL of pristine into the abdominal cavity two weeks ago. The ascites was collected every second day after one week from the administration and was subjected to centrifugal treatment to acquire supernatant. The supernatant was mixed with equal parts of an adsorption buffer solution (3 mol/L NaCl, 1.5 mol/L Glycine-NaOH buffer solution, pH 8.5) and then filtrated. The filtrate was passed through a Protein A Sepharose column equilibrated with the adsorption buffer solution and the antibody in the filtrate was adsorbed with the column and then eluted in a 0.1 mol/L citrate buffer solution (pH 3.0). The eluate was neutralized with a 1 mol/L Tris-HCl buffer solution (pH 9.0) and dialyzed with PBS to collect the purified antibody. Among the monoclonal antibodies produced by the hybridomas acquired as described above, two types of antibodies highly reactive with CRP were used as #08209 and #08210 for the following examples.

Example 2

1) Production of anti-CRP antibody-sensitized conjugate (conjugate in which an anti-CRP monoclonal antibody is immobilized to colloidal gold particles) and anti-hemoglobin antibody-sensitized conjugate (conjugate in which an anti-hemoglobin monoclonal antibody is immobilized to colloidal gold particles)

The anti-CRP monoclonal antibody (Clone: #08210) and the anti-hemoglobin monoclonal antibody (Clone: #69202) were prepared to have the following buffer solution conditions and antibody concentrations. The CRP monoclonal antibody (Clone: #08210) was added as 10 mL of the antibody solution to 200 mL of a 1 OD/ml colloidal gold solution (particle size: 30 nm); the anti-hemoglobin monoclonal antibody (Clone: #69202) was added as 10 mL of the antibody solution to 200 mL of a 1 OD/ml colloidal gold solution (particle size: 40 nm); and the mixtures were stirred at room temperature for 10 minutes. After the addition of 20 ml of a 10% bovine serum albumin (BSA) aqueous solution to the colloidal gold particle-antibody mixtures, the mixtures were further stirred for 5 minutes, and centrifuged at 10,000 rpm at 10 degrees C. for 45 minutes to obtain sediments (an anti-CRP antibody sensitized conjugate and an anti-hemoglobin antibody sensitized conjugate). To each of the acquired conjugates, 12 mL of Conjugate Dilution Buffer (manufactured by Scripps) was added to suspend the conjugates. The absorbance of each of the conjugates was measured at the maximum absorption wavelength.

i) #08210 (20 µg/mL), 2 mmol/L phosphate buffer solution pH 7.0
   ii) #69202 (80 µg/mL), 2 mmol/L borate buffer solution pH 9.0

2) Production of conjugate pad

The anti-CRP antibody-sensitized conjugate and anti-hemoglobin antibody-sensitized conjugate produced in (1) were mixed at 15 OD/ml and 10 OD/ml, respectively, with a 20 mmol/L Tris-HCl buffer solution (pH 7.5) containing a 1.33% casein and 4% sucrose solution to prepare a conjugate solution. A glass fiber pad having a certain volume (No. 8964 manufactured by Pall Corporation) was impregnated with 1.2 volumes (relative to the volume of the pad) of the conjugate solution. The pad was dried at 70 degrees C. for 30 minutes in a dry oven to obtain a conjugate pad. If an additive such as a sensitizer is added as needed, a necessary amount may be added to the conjugate solution before performing the operation above.

3) Production of insoluble membrane support having anti-CRP antibody and anti-hemoglobin antibody immobilized (antibody immobilized membrane)

The membrane was produced as is the case with Example 1 except that Clone #08210 was used as the anti-CRP antibody instead of Clone FERM BP-11344.

4) Production of sample pad

The sample pad was produced as is the case with Example 1.

5) Production of test strip

The test strip was produced as is the case with Example 1 except that the antibody-immobilized membrane of 3) in Example 2 was used as the antibody-immobilized membrane. The acquired test strip was turned to a form of the immunochromatographic test device as is the case with Example 1.

6) Production of calibration curve for hematocrit value (HCT value) calculation

Certified Practical Reference Material for Total Hemoglobin Measurement (JCCRM 622-1) was used to prepare 40.4 g/L, 80.7 g/L, 136.7 g/L, 185.7 g/L, and 273.4 g/L hemoglobin reference solutions and each of the reference solutions was diluted with a 0.01% Tween 20 and 10 mmol/L phosphate buffer solution (pH 7.2) by a factor of 151. From each of the solutions, 120 µl, was dripped to the sample supply window of the immunochromatographic test device to measure the reflected light intensity of the Hb measurement line from the detection window of the immunochromatographic test device after five minutes by using the immunochromatography reader ICA-1000 (manufactured by Hamamatsu Photonics K.K.). The calibration curve for HCT value calculation was produced with the Y-axis indicative of an HCT value (%) acquired by multiplying the hemoglobin concentration (g/L) of each of the reference solutions by 2.9/10, and the X-axis indicative of the reflected light intensity of the Hb measurement line (FIG. 8).

7) Production of calibration curve of CRP measurement

A dilution series of 0, 3, 10, 30, 60, 120, 210, and 420 mg/L was prepared by diluting a 420 mg/L standard preparation of CRP calibrator D for Nanopia (manufactured by Sekisui Medical Co., Ltd.) with a 0 mg/L standard preparation. Each was diluted with a 0.01% Tween 20 and 10 mmol/L phosphate buffer solution (pH 7.2) by a factor of 151, and 120 µL of the sample was dripped to the sample supply window of the test device to measure the reflected light intensity of the CRP measurement line from the detection window of the immunochromatographic test device after five minutes by using the immunochromatography reader ICA-1000 (manufactured by Hamamatsu Photonics K.K.). FIG. 9 depicts a calibration curve in a range of CRP concentrations from 0 to 420 mg/L.

8) Calculation of CRP and HCT value using immunochromatographic test strip of the present invention The measurement of 200 specimens was performed by using the immunochromatographic test device described above. Specifically, 10 µL of each blood was diluted and hemolyzed with a 0.01% Tween 20 and 10 mmol/L phosphate buffer solution (pH 7.2) by a factor of 150, and 120 µL of the sample was dripped to the sample supply window of the immunochromatographic test device to measure the reflected light intensities of the CRP measurement line and the Hb measurement line from the detection window of the immunochromatographic test device after five minutes by using the immunochromatography reader ICA-1000 (manufactured by Hamamatsu Photonics K.K.).

The reflected light intensity of the Hb measurement line was extrapolated to the calibration curve of FIG. 8 to obtain the HCT value (%) and the reflected light intensity of the CRP measurement line was extrapolated to the calibration curve of FIG. 9 to obtain the CRP concentration. The CRP concentration after HCT correction was calculated with the following equation.

$$\text{corrected } CRP \text{ measurement value} = \frac{\text{uncorrected } CRP \text{ measurement value}}{(1 - \text{calculated HCT value (\%)}/100)}$$

9) Verification of effect of HCT correction of the present invention

The CRP concentrations in plasma of the 200 blood specimens were measured by using a commercially available kit based on the measurement principle of a latex agglutination reaction (Nanopia CRP manufactured by Sekisui Medical Co., Ltd.).

FIG. 10 depicts correlation between the "CRP measurement value" of Nanopia CRP and the CRP concentration before HCT correction calculated in 8) of this example, i.e., "CRP measurement value (without HCT correction)". FIG. 11 depicts correlation between the "CRP measurement value" of Nanopia CRP and the HCT-corrected CRP concentration calculated in 8) of this example, i.e., "CRP measurement value (with HCT correction, the present invention)".

In the case of the "CRP measurement value (without HCT correction)" not subjected to the hematocrit correction, a slope of a correlation regression equation relative to the commercially available CRP measurement kit was about 0.62 and $R^2$ was about 0.930 while in the case of the "CRP measurement value (with HCT correction)" subjected to the hematocrit correction of the present invention, the slope was about 0.99 and $R^2$ was about 0.968, and the improvement in correlation was recognized.

From these results, it was demonstrated that the CRP measurement can more accurately be performed by measuring the concentrations of CRP and hemoglobin in the same measurement sample according to the present invention by using a reagent for immunochromatography, and by performing the hematocrit correction of the CRP measurement value by utilizing the correlation relationship between the measurement value of hemoglobin and the hematocrit value in the sample.

Example 3

Four types of immunochromatographic test devices were produced in the same way as 1) to 5) of Example 1, except that, when the antibody-immobilized membrane of 3) is produced, Clone 08209 was used instead of using Clone FERM BP-11345 as the anti-CRP antibody and that the capillary flow time of the membrane was changed to 19 seconds/cm (SHF75), 30 seconds/cm (SHF120), 45 seconds/cm (SHF180), and 60 seconds/cm (SHF240).

Certified Practical Reference Material for Total Hemoglobin Measurement [JCCRM 622-1L (80.7 g/L), 1 mol/L (136.7 g/L), 1H185.7 g/L)] was diluted with a 0.01% Tween 20 and 10 mmol/L phosphate buffer solution (pH 7.2) by a factor of 151, and 120 μL of each of the solutions was dripped to the sample supply windows of the four types of the immunochromatographic test devices to measure the reflected light intensity of the Hb measurement line from the detection windows of the devices after five minutes by using the immunochromatography reader ICA-1000 (manufactured by Hamamatsu Photonics K.K.). The calibration curve for HCT value calculation was produced with the Y-axis indicative of an HCT value (%) acquired by multiplying the hemoglobin concentration (g/L) of each of the reference solutions by 2.9/10, and the X-axis indicative of the reflected light intensity of the Hb measurement line (FIG. 12).

It was found out that, as the capillary flow time of the membrane decreased, and thus, the flow rate increased, the change in the reflected light intensity was reduced relative to the change in the HCT value. When the capillary flow time decreased to 19 seconds/cm, little change is made in the reflected light intensity even if the HCT value changed. It is thought that this result is generated because the principle of the Hb measurement of the present invention is based on a competitive reaction between free Hb not bound to the anti-Hb antibody and Hb bound to the anti-Hb antibody on the colloidal gold particles. It is probably thought that, if the flow rate becomes higher, the free Hb reaches the Hb measurement line first and fills all the Hb binding sites of the anti-Hb antibody on the Hb measurement line. From these results, it is known that the capillary flow time of the membrane is preferably 30 seconds/cm to 60 seconds/cm.

REFERENCE SIGNS LIST (a) adhesive plastic sheet
(b) antibody-immobilized membrane
(c) anti-CRP antibody
(d) anti-hemoglobin antibody
(e) conjugate pad
(f) sample pad
(g) absorbent pad
(h) polyester film
(i) 3rd pad

REFERENCE TO DEPOSITED BIOLOGICAL MATERIAL

Accession numbers
FERM BP-11344
FERM BP-11345

(1) FERM BP-11344 (#08202 producing hybridoma)
i) Name and address of depository institution at which the biological materials were deposited.
International Patent Organism Depositary, National Institute of Advanced Industrial Science and Technology
Tsukuba Central 6, 1-1-1 Higashi, Tsukuba, Ibaraki 305-8566, Japan
ii) Date of biological material deposit in the depository institution in i).
Nov. 26, 2009
iii) Accession number for the deposition assigned by the depository institution in i).
FERM BP-11344

(2) FERM BP-11345 (#08203 producing hybridoma)
i) Name and address of depository institution at which the biological materials were deposited.
International Patent Organism Depositary, National Institute of Advanced Industrial Science and Technology
Tsukuba Central 6, 1-1-1 Higashi, Tsukuba, Ibaraki 305-8566, Japan
ii) Date of biological material deposit in the depository institution in i).
Nov. 26, 2009
iii) Accession number for the deposition assigned by the depository institution in i).
FERM BP-11345

The invention claimed is:
1. A method of measuring an analyte and hemoglobin in a sample by immunochromatography, comprising the following steps A to D, wherein the sample is a blood sample hemolyzed and diluted by a factor of 50 to 400:

A. a step of measuring hemoglobin in the sample by competitive immunochromatography using 1) and 2) described below,
1) a conjugate in which a first antibody against hemoglobin is immobilized to a first label, and
2) an insoluble membrane support to which a second antibody against hemoglobin is immobilized, wherein if an epitope of the first antibody against hemoglobin is monovalent, an epitope of the second antibody is different from an epitope of the first antibody, while if an epitope of the first antibody is multivalent, an epitope of the second antibody may be the same as an epitope of the first antibody or the first antibody may be the same as the second antibody;
B. a step of measuring the analyte in the sample by immunochromatography using 5) and 6) described below,
5) a conjugate in which a first antibody against the analyte is immobilized to a second label, and
6) an insoluble membrane support to which a second antibody against the analyte is immobilized, wherein if an epitope of the first antibody against the analyte is monovalent, an epitope of the second antibody is different from an epitope of the first antibody, while if an epitope of the first antibody is multivalent, an epitope of the second antibody may be the same as an epitope of the first antibody or the first antibody may be the same as the second antibody;
C. a step of obtaining a hematocrit value of the sample from a measurement value of hemoglobin acquired at the step A; and
D. a step of correcting a measurement value of the analyte acquired at the step B by using the hematocrit value acquired at the step C, and
wherein the steps A and B are performed in the same flow passage.

2. The method of claim 1, wherein the analyte is selected from a group consisting of inflammation-related markers; coagulation or fibrinolysis markers; cardiovascular-related markers; metabolism-related markers; tumor markers; infectious disease-related markers; and allergen-specific IgE (immunoglobulin E).

3. An immunochromatographic test strip for measuring an analyte and hemoglobin in a sample by immunochromatography, the immunochromatographic test strip comprising the following E and F:
E. a section for measuring hemoglobin including 1) and 2) described below,
1) a conjugate in which a first antibody against hemoglobin is immobilized to a first label, and
2) an insoluble membrane support to which a second antibody against hemoglobin is immobilized, wherein if an epitope of the first antibody against hemoglobin is monovalent, an epitope of the second antibody is different from an epitope of the first antibody, while if an epitope of the first antibody is multivalent, an epitope of the second antibody may be the same as an epitope of the first antibody or the first antibody may be the same as the second antibody); and
F. a section for measuring the analyte including 5) and 6) described below,
5) a conjugate in which a first antibody against the analyte is immobilized to a second label, and
6) an insoluble membrane support to which a second antibody against the analyte is immobilized, wherein if an epitope of the first antibody against the second analyte is monovalent, an epitope of the second antibody is different from the first antibody, while if an epitope of the first antibody is multivalent, an epitope of the second antibody may be the same as an epitope of the first antibody or the first antibody may be the same as the second antibody;
wherein E and F are disposed in the same flow passage, and
wherein the analyte is selected from a group consisting of: inflammation-related markers; coagulation or fibrinolysis markers; cardiovascular-related markers; metabolism-related markers; tumor markers; infectious disease-related markers; and allergen-specific IgE (immunoglobulin E).

4. The immunochromatographic test strip of claim 3, further comprising the following G and H, wherein the conjugates of 1) of E and 5) of F are contained in a conjugate pad and disposed on the upstream side of the insoluble membrane support of 2) of E and 6) of F,
G. a sample pad located on the upstream side of a conjugate pad adapted to be supplied with a sample, and
H. an absorbent pad located on the downstream side of the insoluble membrane support of 2) of E and 6) of F.

5. An assay reagent kit for immunochromatography comprising: the immunochromatographic test strip of claim 3 or 4; and a diluting solution for hemolysis and dilution.

6. A method for measuring an analyte and hemoglobin in a sample by immunochromatography, comprising the step of:
applying a sample which is blood hemolyzed and diluted by a factor of 50 to 400 to an immunochromatographic test device, said immunochromatographic test strip comprising the following E and F:
E. a section for measuring hemoglobin including 1) and 2) described below,
1) a conjugate in which a first antibody against hemoglobin is immobilized to a first label, and
2) an insoluble membrane support to which a second antibody against hemoglobin is immobilized, wherein if an epitope of the first antibody against hemoglobin is monovalent, an epitope of the second antibody is different from an epitope of the first antibody, while if the first antibody is multivalent, an epitope of the second antibody may be the same as an epitope of the first antibody; and
F. the section also for measuring the analyte including 5) and 6) described below,
5) a conjugate in which a first antibody against the analyte is immobilized to a second label, and
6) an insoluble membrane support to which a second antibody against the analyte is immobilized, wherein if an epitope of the first antibody against the analyte is monovalent, an epitope of the second antibody is different from an epitope of the first antibody, while if the first antibody is multivalent, an epitope of the second antibody may be the same as an epitope of the first antibody, and
wherein E and F are disposed in the same flow passage.

7. The method of claim 6, wherein the immunochromatographic test strip further comprises the following G and H, wherein a conjugate pad is disposed on the upstream side of the insoluble membrane support of 2) of E and 6) of F,
G. a sample pad located on the upstream side of the conjugate pad and adapted to be supplied with a sample, and
H. an absorbent pad located on the downstream side of the insoluble membrane support 2) of E and 6) of F.

8. The method of claim 1, wherein the analyte is selected from a group consisting of: inflammation-related markers C-reactive protein (CRP), IgA, IgG, and IgM; coagulation or fibrinolysis markers fibrin degradation products D-dimer, soluble fibrin, TAT (thrombin-antithrombin complex), and PIC (plasmin-plasmin inhibitor complex); cardiovascular-related markers oxidized LDL and BNP (brain natriuretic peptide); metabolism-related marker adiponectin; tumor markers CEA (carcinoembryonic antigen), AFP (a-fetoprotein), CA19-9, CA125, and PSA (prostate-specific antigen); infectious disease-related markers HBV (hepatitis B virus) and HCV (hepatitis C virus); and allergen-specific IgE (immunoglobulin E).

9. The method of claim 1, wherein the insoluble membrane support to which the second antibody against hemoglobin is immobilized and the insoluble membrane support to which the second antibody against the analyte is immobilized are the same insoluble membrane support and wherein the second antibody against hemoglobin is immobilized at a location within said insoluble membrane support that is different from a location to which the second antibody against the analyte is immobilized.

10. The immunochromatographic test strip of claim 3, wherein the insoluble membrane support to which the second antibody against hemoglobin is immobilized and the insoluble membrane support to which the second antibody against the analyte is immobilized are the same insoluble membrane support and wherein the second antibody against hemoglobin is immobilized at a location within said insoluble membrane support that is different from a location to which the second antibody against the analyte is immobilized.

11. The method of claim 6, wherein the insoluble membrane support to which the second antibody against hemoglobin is immobilized and the insoluble membrane support to which the second antibody against the analyte is immobilized are the same insoluble membrane support and wherein the second antibody against hemoglobin is immobilized at a location within said insoluble membrane support that is different from a location to which the second antibody against the analyte is immobilized.

12. The method of claim 1, wherein a sample pad is upstream of the insoluble membrane support.

13. The method of claim 1, wherein a conjugate pad is partially disposed on the insoluble membrane support at the upstream end of the insoluble membrane support.

14. The method of claim 1, wherein an absorbent pad is partially disposed on the insoluble membrane at the downstream end of the insoluble membrane support.

15. The immunochromatographic test strip of claim 3, wherein a sample pad is upstream of the insoluble membrane support.

16. The immunochromatographic test strip of claim 3, wherein a conjugate pad is partially disposed on the insoluble membrane support at the upstream end of the insoluble membrane support.

17. The immunochromatographic test strip of claim 3, wherein an absorbent pad is partially disposed on the insoluble membrane at the downstream end of the insoluble membrane support.

18. The method of claim 6, wherein a sample pad is upstream of the insoluble membrane support.

19. The method of claim 6, wherein a conjugate pad is partially disposed on the insoluble membrane support at the upstream end of the insoluble membrane support.

20. The method of claim 6, wherein an absorbent pad is partially disposed on the insoluble membrane at the downstream end of the insoluble membrane support.

21. The method of claim 1, wherein the sample is a blood sample hemolyzed and diluted by a factor of 50 to 200.

22. The method of claim 1, wherein the sample is a blood sample hemolyzed and diluted by a factor of 50 to 100.

23. The method of claim 1, wherein the sample is a blood sample hemolyzed and diluted by a factor of 100.

24. The method of claim 6, wherein the sample is a blood sample hemolyzed and diluted by a factor of 50 to 200.

25. The method of claim 6, wherein the sample is a blood sample hemolyzed and diluted by a factor of 50 to 100.

26. The method of claim 6, wherein the sample is a blood sample hemolyzed and diluted by a factor of 100.

* * * * *